(12) United States Patent
Kim et al.

(10) Patent No.: US 10,214,766 B2
(45) Date of Patent: Feb. 26, 2019

(54) LUMINESCENT SUBSTRATE FOR USE IN ARTIFICIAL BIOLUMINESCENT ENZYME

(71) Applicant: NATIONAL INSTITUTE OF ADVANCED INDUSTRIAL SCIENCE AND TECHNOLOGY, Tokyo (JP)

(72) Inventors: Sung Bae Kim, Tsukuba (JP); Hiroshi Izumi, Tsukuba (JP); Hiroaki Tao, Tsukuba (JP); Masaki Torimura, Tsukuba (JP); Akihiro Wakisaka, Tsukuba (JP)

(73) Assignee: NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 39 days.

(21) Appl. No.: 15/030,281

(22) PCT Filed: Oct. 16, 2014

(86) PCT No.: PCT/JP2014/077618
§ 371 (c)(1),
(2) Date: Apr. 18, 2016

(87) PCT Pub. No.: WO2015/056762
PCT Pub. Date: Apr. 23, 2015

(65) Prior Publication Data
US 2016/0281129 A1 Sep. 29, 2016

(30) Foreign Application Priority Data
Oct. 18, 2013 (JP) ................. 2013-217560

(51) Int. Cl.
C12Q 1/66 (2006.01)
C07D 241/38 (2006.01)
C12N 9/02 (2006.01)
C07D 487/04 (2006.01)

(52) U.S. Cl.
CPC ............ *C12Q 1/66* (2013.01); *C07D 241/38* (2013.01); *C07D 487/04* (2013.01); *C12N 9/0069* (2013.01); *C12Y 113/12* (2013.01); *C12Y 113/12007* (2013.01)

(58) Field of Classification Search
CPC ............... C07K 14/72; C07K 2319/21; C07K 2319/41; C07K 2319/42; C07K 2319/43; C07K 2319/61; C07K 2319/70; C12N 9/0069; C12Q 1/66; C12Q 1/6897; C12Y 113/12007; G01N 33/535; G01N 33/581
See application file for complete search history.

(56) References Cited

U.S. PATENT DOCUMENTS

| | | | |
|---|---|---|---|
| 8,043,827 B2 | 10/2011 | Kim et al. | |
| 8,124,424 B2 | 2/2012 | Umezawa et al. | |
| 2004/0219527 A1 | 11/2004 | Golz et al. | |
| 2009/0123954 A1 | 5/2009 | Kim et al. | |
| 2009/0233320 A1 | 9/2009 | Takenaka | |
| 2009/0269781 A1 | 10/2009 | Kim et al. | |
| 2010/0273150 A1 | 10/2010 | Umezawa et al. | |
| 2012/0034672 A1 | 2/2012 | Kim et al. | |
| 2012/0035070 A1 | 2/2012 | Inouye et al. | |
| 2012/0258465 A1 | 10/2012 | Inouye et al. | |
| 2013/0273582 A1* | 10/2013 | Daly | C12N 9/0069 435/8 |
| 2014/0024058 A1 | 1/2014 | Inouye et al. | |
| 2014/0296521 A1 | 10/2014 | Inouye et al. | |
| 2015/0284813 A1 | 10/2015 | Kim et al. | |
| 2015/0344936 A1 | 12/2015 | Inouye et al. | |

FOREIGN PATENT DOCUMENTS

| | | |
|---|---|---|
| JP | 2004-516828 A | 6/2004 |
| JP | 2009-034059 A | 2/2009 |
| JP | 2011-067190 A | 4/2011 |
| JP | 2012-217357 A | 11/2012 |
| WO | WO 2006/061906 A1 | 6/2006 |
| WO | WO 2008/084869 A1 | 7/2008 |
| WO | WO 2010/090319 A1 | 8/2010 |
| WO | WO 2010/119721 A1 | 10/2010 |
| WO | WO 2011/102178 A1 | 8/2011 |
| WO | WO 2012/071631 A1 | 6/2012 |
| WO | WO 2014/065047 A1 | 5/2014 |

OTHER PUBLICATIONS

Shimomura, O. (2006).Bioluminescence: Chemical principles and methods. (pp. 1-29). Singapore: World Scientific. https://doi.org/10.1142/6102. (Year: 2006).*
Kim et al. (2012) Bioconjugate Chemistry 23(11): 2221-2228. (Year: 2012).*
Kim et al. (2013) Bioconjugate Chemistry 24(12): 2067-2075. (Year: 2013).*
Kim et al. (2014) Biochemical and Biophysical Research Communications 448(4): 418-423. (Year: 2014).*
Kim et al. (2017) Combinatorial Science 19(9): 594-599. (Year: 2017).*
Hall et al., *ACS Chemical Biology*, 7: 1848-1857 (2012).
Herring et al., *Marine Ecology Progress Series*, 94: 297-309 (1993).

(Continued)

*Primary Examiner* — Lisa J Hobbs
(74) *Attorney, Agent, or Firm* — Leydig, Voit & Mayer, Ltd.

(57) ABSTRACT

The invention relates to a bioluminescent substrate suitably usable in a series of artificial luciferases (ALuc), and the invention provides a wavelength-shifted spectrum with a selective high intensity luminescence and high luminescence stability obtained by the use of the substrate together with ALuc. The luminescent substrate for ALuc obtained by the invention can be included together with a suitable luminescence solution in a luminescence kit. The bioluminescent substrate for ALuc of the invention can exhibit unprecedented excellent luminescence specificity and functionality in the conventional bioluminescence probe, two-hybrid assay, bioluminescent capsule, and reporter gene assay.

8 Claims, 8 Drawing Sheets
Specification includes a Sequence Listing.

(56) References Cited

OTHER PUBLICATIONS

Inoue et al., *Chemistry Letters*, 141-144 (1975).
Inoue et al., *Tetrahedron Letters*, 31: 2685-2688 (1977).
Inouye et al., *Biochemical and Biophysical Research Communication*, 365: 96-101 (2008).
Izumi et al., *Journal of Chemical Information and Modeling*, 53(3): 584-591 (2013).
Jones et al., *Synlett*, 6: 509-510 (1996).
Kim et al., *ACS Chemical Biology*, 3(6): 359-372 (2008).
Kim et al., *Analytical Chemistry*, 83: 8732-8740 (2011).
Kim et al., *Analytical Chemistry*, 77(20): 6588-6593 (2005).
Kim et al., *Analytical Chemistry*, 79(5): 1874-1880 (2007).
Kim et al., *Analytical Chemistry*, 79(13): 4820-4826 (2007).
Kim et al., *Bioconjugate Chemistry*, 19(12): 2480-2486 (2008).
Kim et al., *Bioconjugate Chemistry*, 22: 1835-1841 (2011).
Kim, Sung Bae, *Protein Engineering, Design & Selection*, 25(6): 261-269 (2012).
Kim et al., "Methods of Analysis for Imaging and Detecting Ions and Molecules" (Chapter 13) in *Cellular and Biomolecular Recognition: Synthetic and Non-Biological Molecules*, pp. 301-340 (Wiley-VCH, 2009).
Kim et al., *PNAS*, 101(32): 11542-11547 (2004).
Kim et al., *The Chemical Society of Japan Dai 93 Shunki Taikai*, 93(2): 410, abstract 2G1-44 (2013).
Kishi et al., *Tetrahedron Letters*, 13(27): 2747-2748 (1972).
Lehman et al., *Protein Engineering*, 15(5): 403-411 (2002).
Li et al., *Appln. Microbiol. Biotechnol.*, 85: 909-919 (2010).
Loening et al., *Nature Methods*, 4(8): 641-643 (2007).
Markova et al., *The Journal of Biological Chemistry*, 279(5): 3212-3217 (2004).
Michnick et al., *Methods in Enzymology*, 470: 335-368 (2010).
Nakamura et al., *Synlett*, 12: 1227-1228 (1995).
Niu et al., *Theranostics*, 2(4): 413-423 (2012).
Okita et al., *Nature*, 448: 313-317 (2007).
Shimomura et al., *Biochem. J.*, 251: 405-410 (1988).
Takenaka et al., *Gene*, 425: 28-35 (2008).
Takenaka et al., *Mol. Biol., Evol.*, 29(6): 1669-1681 (2012).
Teranishi et al., *Analytical Biochemistry*, 249: 37-43 (1997).
Teranishi et al., *Bull. Chem. Soc. Japan.*, 63(11): 3132-3140 (1990).
Verhaegen et al., *Anal. Chem.*, 74(17): 4378-4385 (2002).
Wu et al., *Bio Techniques*, 42(3): 290-292 (2007).
Wu et al., *Tetrahedron Letters*, 42: 2997-3000 (2001).
Japanese Patent Office, International Search Report in International Patent Application No. PCT/JP2014/077618 (dated Jan. 6, 2015).

\* cited by examiner (B)

[Monochrome inversion image]

Relative Optical Intensity
(Image guage, FujiFilm)

SEQUENCE LISTING

<160> NUMBER OF SEQ ID NOS: 58

<210> SEQ ID NO 1
<211> LENGTH: 221
<212> TYPE: PRT
<213> ORGANISM: Artificial Sequence
<220> FEATURE:
<223> OTHER INFORMATION: Synthetic Sequence -continued

```
<220> FEATURE:
<221> NAME/KEY: MISC_FEATURE
<222> LOCATION: (3)..(7)
<223> OTHER INFORMATION: Xaa(3)=any a.a. Xaa(5)=hydrophobic a.a.
      Xaa(4,6,7)=aliphatic a.a.
<220> FEATURE:
<221> NAME/KEY: MISC_FEATURE
<222> LOCATION: (10)..(11)
<223> OTHER INFORMATION: Xaa(10,11)=aliphatic a.a.
<220> FEATURE:
<221> NAME/KEY: MISC_FEATURE
<222> LOCATION: (13)..(13)
<223> OTHER INFORMATION: Xaa=hydrophobic a.a.
<220> FEATURE:
<221> NAME/KEY: MISC_FEATURE
<222> LOCATION: (15)..(16)
<223> OTHER INFORMATION: Xaa(16)=hydrophobic a.a. Xaa(15)=aliphatic a.a.
<220> FEATURE:
<221> NAME/KEY: MISC_FEATURE
<222> LOCATION: (20)..(29)
<223> OTHER INFORMATION: Xaa(20,21,24-29-29)=any a.a. Xaa(22,23)=any or
      no a.a.
<220> FEATURE:
<221> NAME/KEY: MISC_FEATURE
<222> LOCATION: (31)..(35)
<223> OTHER INFORMATION: Xaa(31,32,35)=any a.a. Xaa(33,34)=aliphatic
      a.a.
<220> FEATURE:
<221> NAME/KEY: MISC_FEATURE
<222> LOCATION: (37)..(37)
<223> OTHER INFORMATION: Xaa(37)=any a.a.
<220> FEATURE:
<221> NAME/KEY: MISC_FEATURE
<222> LOCATION: (39)..(41)
<223> OTHER INFORMATION: Xaa(39,40)=aliphatic or no a.a. Xaa(41)=
      aliphatic a.a.
<220> FEATURE:
<221> NAME/KEY: MISC_FEATURE
<222> LOCATION: (62)..(69)
<223> OTHER INFORMATION: Xaa(64-66,69)=any a.a. Xaa(67)=hydrophobic a.a.
      Xaa(63,68)=aliphatic a.a. Xaa(62)=negative a.a.
<220> FEATURE:
<221> NAME/KEY: MISC_FEATURE
<222> LOCATION: (72)..(78)
<223> OTHER INFORMATION: Xaa(76,77)=any or no a.a. Xaa(75)=hydrophilic
      a.a. Xaa(74)=aliphatic or no a.a. Xaa(78)=aliphatic a.a.
      Xaa(72,73)=positive or no a.a.
<220> FEATURE:
<221> NAME/KEY: MISC_FEATURE
<222> LOCATION: (83)..(83)
<223> OTHER INFORMATION: Xaa=aliphatic a.a.
<220> FEATURE:
<221> NAME/KEY: MISC_FEATURE
<222> LOCATION: (85)..(86)
<223> OTHER INFORMATION: Xaa(85,86)=any a.a.
<220> FEATURE:
<221> NAME/KEY: MISC_FEATURE
<222> LOCATION: (89)..(90)
<223> OTHER INFORMATION: Xaa(89,90)=any a.a.
<220> FEATURE:
<221> NAME/KEY: MISC_FEATURE
<222> LOCATION: (97)..(97)
<223> OTHER INFORMATION: Xaa=positive a.a.
<220> FEATURE:
<221> NAME/KEY: MISC_FEATURE
<222> LOCATION: (101)..(101)
<223> OTHER INFORMATION: Xaa=hydrophilic a.a.
<220> FEATURE:
<221> NAME/KEY: MISC_FEATURE
<222> LOCATION: (110)..(110)
<223> OTHER INFORMATION: Xaa=positive a.a.
<220> FEATURE:
<221> NAME/KEY: MISC_FEATURE
<222> LOCATION: (119)..(119)
<223> OTHER INFORMATION: Xaa=hydrophilic a.a.
<220> FEATURE:
<221> NAME/KEY: MISC_FEATURE
<222> LOCATION: (129)..(129)
<223> OTHER INFORMATION: Xaa=any a.a.
```

```
<220> FEATURE:
<221> NAME/KEY: MISC_FEATURE
<222> LOCATION: (137)..(137)
<223> OTHER INFORMATION: Xaa=aliphatic a.a.
<220> FEATURE:
<221> NAME/KEY: MISC_FEATURE
<222> LOCATION: (140)..(144)
<223> OTHER INFORMATION: Xaa(140)=any or no a.a. Xaa(141-144)=any a.a.
<220> FEATURE:
<221> NAME/KEY: MISC_FEATURE
<222> LOCATION: (148)..(151)
<223> OTHER INFORMATION: Xaa(148-151)=any or no a.a.
<220> FEATURE:
<221> NAME/KEY: MISC_FEATURE
<222> LOCATION: (159)..(161)
<223> OTHER INFORMATION: Xaa(159,161)=any a.a. Xaa(160)=aliphatic a.a.
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: MISC_FEATURE
<222> LOCATION: (188)..(188)
<223> OTHER INFORMATION: Xaa=any a.a.
<220> FEATURE:
<221> NAME/KEY: MISC_FEATURE
<222> LOCATION: (191)..(191)
<223> OTHER INFORMATION: Xaa=any a.a.
<220> FEATURE:
<221> NAME/KEY: MISC_FEATURE
<222> LOCATION: (202)..(203)
<223> OTHER INFORMATION: Xaa(202)=any a.a. Xaa(203)=aliphatic a.a.
<220> FEATURE:
<221> NAME/KEY: MISC_FEATURE
<222> LOCATION: (206)..(206)
<223> OTHER INFORMATION: Xaa(206)=any a.a.
<220> FEATURE:
<221> NAME/KEY: MISC_FEATURE
<222> LOCATION: (211)..(211)
<223> OTHER INFORMATION: Xaa=negative a.a.
<220> FEATURE:
<221> NAME/KEY: MISC_FEATURE
<222> LOCATION: (214)..(214)
<223> OTHER INFORMATION: Xaa(214)=hydrophilic a.a.
<220> FEATURE:
<221> NAME/KEY: MISC_FEATURE
<222> LOCATION: (218)..(218)
<223> OTHER INFORMATION: Xaa=hydrophobic a.a.

<400> SEQUENCE: 1

Met Met Xaa Xaa Xaa Xaa Xaa Phe Ala Xaa Xaa Cys Xaa Ala Xaa Xaa
1               5                   10                  15

Gln Ala Asn Xaa Xaa Xaa Xaa Xaa Xaa Xaa Xaa Asp Xaa Xaa
            20                  25                  30

Xaa Xaa Xaa Gly Xaa Phe Xaa Xaa Xaa Asp Leu Glu Thr Asp Leu Phe
        35                  40                  45

Thr Ile Val Glu Asp Met Asn Val Ile Ser Arg Asp Thr Xaa Xaa Xaa
    50                  55                  60

Xaa Xaa Xaa Xaa Xaa Arg Gly Xaa Xaa Xaa Xaa Xaa Xaa Pro Gly
65                  70                  75                  80

Lys Lys Xaa Pro Xaa Xaa Val Leu Xaa Xaa Leu Glu Ala Asn Ala Gln
            85                  90                  95

Xaa Ala Gly Cys Xaa Arg Gly Cys Leu Ile Cys Leu Ser Xaa Ile Lys
            100                 105                 110

Cys Thr Ala Lys Met Lys Xaa Trp Leu Pro Gly Arg Cys Glu Ser Trp
            115                 120                 125

Xaa Gly Asp Lys Glu Thr Gly Gln Xaa Gly Ile Xaa Xaa Xaa Xaa Xaa
    130                 135                 140
```

```
Val Asp Ile Xaa Xaa Xaa Xaa Pro Glu Ile Pro Gly Phe Lys Xaa Xaa
145                 150                 155                 160

Xaa Pro Met Glu Gln Phe Ile Ala Gln Val Asp Leu Cys Xaa Asp Cys
                165                 170                 175

Thr Thr Gly Cys Leu Lys Gly Leu Ala Asn Val Xaa Cys Ser Xaa Leu
                180                 185                 190

Leu Lys Lys Trp Leu Pro Ser Arg Cys Xaa Xaa Phe Ala Xaa Lys Ile
        195                 200                 205

Gln Ala Xaa Val Asp Xaa Ile Lys Gly Xaa Gly Gly Ser
        210                 215                 220

<210> SEQ ID NO 2
<211> LENGTH: 218
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (3)..(7)
<223> OTHER INFORMATION: Xaa(3)=any a.a..
      Xaa(4,6,7)=aliphatic a.a. Xaa(5)=hydrophilic a.a.
<220> FEATURE:
<221> NAME/KEY: MISC_FEATURE
<222> LOCATION: (10)..(11)
<223> OTHER INFORMATION: Xaa(10,11)=aliphatic a.a.
<220> FEATURE:
<221> NAME/KEY: MISC_FEATURE
<222> LOCATION: (13)..(13)
<223> OTHER INFORMATION: Xaa=hydrophobic a.a.
<220> FEATURE:
<221> NAME/KEY: MISC_FEATURE
<222> LOCATION: (15)..(16)
<223> OTHER INFORMATION: Xaa(15)=aliphatic a.a. Xaa(16)=hydrophobic a.a.
<220> FEATURE:
<221> NAME/KEY: MISC_FEATURE
<222> LOCATION: (20)..(27)
<223> OTHER INFORMATION: Xaa(20-27)=any a.a.
<220> FEATURE:
<221> NAME/KEY: MISC_FEATURE
<222> LOCATION: (29)..(39)
<223> OTHER INFORMATION: Xaa(29,30,33)=any a.a.
      Xaa(31,32,37-39)=hydrophilic a.a.
<220> FEATURE:
<221> NAME/KEY: MISC_FEATURE
<222> LOCATION: (60)..(67)
<223> OTHER INFORMATION: Xaa(62-64,67)=any a.a. Xaa(65)=hydrophilic a.a.
      Xaa(61,66)=aliphatic a.a. Xaa(60)=negative a.a.
<220> FEATURE:
<221> NAME/KEY: MISC_FEATURE
<222> LOCATION: (70)..(76)
<223> OTHER INFORMATION: Xaa(74,75)=any or no a.a. Xaa(73)=hydrophilic
      a.a. Xaa(72,76)=aliphatic a.a. Xaa(70,71)=positive a.a.
<220> FEATURE:
<221> NAME/KEY: MISC_FEATURE
<222> LOCATION: (81)..(81)
<223> OTHER INFORMATION: Xaa=aliphatic a.a.
<220> FEATURE:
<221> NAME/KEY: MISC_FEATURE
<222> LOCATION: (83)..(84)
<223> OTHER INFORMATION: Xaa(83,84)=any a.a.
<220> FEATURE:
<221> NAME/KEY: MISC_FEATURE
<222> LOCATION: (87)..(88)
<223> OTHER INFORMATION: Xaa(87,88))=any a.a.
<220> FEATURE:
<221> NAME/KEY: MISC_FEATURE
<222> LOCATION: (95)..(95)
<223> OTHER INFORMATION: Xaa=positive a.a.
<220> FEATURE:
<221> NAME/KEY: MISC_FEATURE
<222> LOCATION: (99)..(99)
<223> OTHER INFORMATION: Xaa=hydrophilic a.a.
```

```
<220> FEATURE:
<221> NAME/KEY: MISC_FEATURE
<222> LOCATION: (108)..(108)
<223> OTHER INFORMATION: Xaa=any a.a.
<220> FEATURE:
<221> NAME/KEY: MISC_FEATURE
<222> LOCATION: (117)..(117)
<223> OTHER INFORMATION: Xaa=hydrophilic a.a.
<220> FEATURE:
<221> NAME/KEY: MISC_FEATURE
<222> LOCATION: (127)..(127)
<223> OTHER INFORMATION: Xaa=any a.a.
<220> FEATURE:
<221> NAME/KEY: MISC_FEATURE
<222> LOCATION: (135)..(135)
<223> OTHER INFORMATION: Xaa=aliphatic a.a.
<220> FEATURE:
<221> NAME/KEY: MISC_FEATURE
<222> LOCATION: (137)..(145)
<223> OTHER INFORMATION: Xaa(137-140)=any or no a.a. Xaa(140-145)=any
     a.a.
<220> FEATURE:
<221> NAME/KEY: MISC_FEATURE
<222> LOCATION: (147)..(148)
<223> OTHER INFORMATION: Xaa(147)=any a.a. Xaa(148)=hydrophobic a.a.
<220> FEATURE:
<221> NAME/KEY: MISC_FEATURE
<222> LOCATION: (156)..(158)
<223> OTHER INFORMATION: Xaa(1596,158)=any a.a. Xaa(157)=aliphatic a.a.
<220> FEATURE:
<221> NAME/KEY: MISC_FEATURE
<222> LOCATION: (171)..(171)
<223> OTHER INFORMATION: Xaa=hydrophobic a.a.
<220> FEATURE:
<221> NAME/KEY: MISC_FEATURE
<222> LOCATION: (185)..(185)
<223> OTHER INFORMATION: Xaa=any a.a.
<220> FEATURE:
<221> NAME/KEY: MISC_FEATURE
<222> LOCATION: (188)..(188)
<223> OTHER INFORMATION: Xaa=any a.a.
<220> FEATURE:
<221> NAME/KEY: MISC_FEATURE
<222> LOCATION: (199)..(200)
<223> OTHER INFORMATION: Xaa(199)=any a.a. Xaa(200)=aliphatic a.a.
<220> FEATURE:
<221> NAME/KEY: MISC_FEATURE
<222> LOCATION: (203)..(203)
<223> OTHER INFORMATION: Xaa=any a.a.
<220> FEATURE:
<221> NAME/KEY: MISC_FEATURE
<222> LOCATION: (208)..(208)
<223> OTHER INFORMATION: Xaa=negative a.a.
<220> FEATURE:
<221> NAME/KEY: MISC_FEATURE
<222> LOCATION: (211)..(211)
<223> OTHER INFORMATION: Xaa=hydrophilic a.a.
<220> FEATURE:
<221> NAME/KEY: MISC_FEATURE
<222> LOCATION: (215)..(215)
<223> OTHER INFORMATION: Xaa=hydrophobic a.a

<400> SEQUENCE: 2

Met Met Xaa Xaa Xaa Xaa Xaa Phe Ala Xaa Xaa Cys Xaa Ala Xaa Xaa
1               5                   10                  15

Gln Ala Asn Xaa Xaa Xaa Xaa Xaa Xaa Xaa Asp Xaa Xaa Xaa Xaa
            20                  25                  30

Xaa Xaa Xaa Xaa Xaa Xaa Xaa Asp Leu Glu Thr Asp Leu Phe Thr Ile
        35                  40                  45

Val Glu Asp Met Asn Val Ile Ser Arg Asp Thr Xaa Xaa Xaa Xaa Xaa
    50                  55                  60

Xaa Xaa Xaa Arg Gly Xaa Xaa Xaa Xaa Xaa Xaa Pro Gly Lys Lys
65                  70                  75                  80
```

```
Xaa Pro Xaa Xaa Val Leu Xaa Xaa Leu Glu Ala Asn Ala Gln Xaa Ala
                85                  90                  95

Gly Cys Xaa Arg Gly Cys Leu Ile Cys Leu Ser Xaa Ile Lys Cys Thr
            100                 105                 110

Ala Lys Met Lys Xaa Trp Leu Pro Gly Arg Cys Glu Ser Trp Xaa Gly
            115                 120                 125

Asp Lys Glu Thr Gly Gln Xaa Gly Xaa Xaa Xaa Xaa Xaa Xaa Xaa Xaa
130                 135                 140

Xaa Val Xaa Xaa Pro Glu Ile Pro Gly Phe Lys Xaa Xaa Xaa Pro Met
145                 150                 155                 160

Glu Gln Phe Ile Ala Gln Val Asp Leu Cys Xaa Asp Cys Thr Thr Gly
                165                 170                 175

Cys Leu Lys Gly Leu Ala Asn Val Xaa Cys Ser Xaa Leu Leu Lys Lys
            180                 185                 190

Trp Leu Pro Ser Arg Cys Xaa Xaa Phe Ala Xaa Lys Ile Gln Ala Xaa
            195                 200                 205

Val Asp Xaa Ile Lys Gly Xaa Gly Gly Ser
210                 215
```

<210> SEQ ID NO 3
<211> LENGTH: 215
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (3)..(7)
<223> OTHER INFORMATION: Xaa(3)=any a.a..
     Xaa(4,6,7)=hydrophobic a.a.
     Xaa(5)=hydrophilic a.a.
<220> FEATURE:
<221> NAME/KEY: MISC_FEATURE
<222> LOCATION: (10)..(11)
<223> OTHER INFORMATION: Xaa=hydrophobic a.a.
<220> FEATURE:
<221> NAME/KEY: MISC_FEATURE
<222> LOCATION: (13)..(13)
<223> OTHER INFORMATION: Xaa=hydrophobic a.a.
<220> FEATURE:
<221> NAME/KEY: MISC_FEATURE
<222> LOCATION: (15)..(16)
<223> OTHER INFORMATION: Xaa=hydrophobic a.a.
<220> FEATURE:
<221> NAME/KEY: MISC_FEATURE
<222> LOCATION: (20)..(20)
<223> OTHER INFORMATION: Xaa=hydrophobic a.a.
<220> FEATURE:
<221> NAME/KEY: MISC_FEATURE
<222> LOCATION: (22)..(22)
<223> OTHER INFORMATION: Xaa=any a.a.
<220> FEATURE:
<221> NAME/KEY: MISC_FEATURE
<222> LOCATION: (24)..(27)
<223> OTHER INFORMATION: Xaa(24,25)=hydophilic a.a.
     Xaa(26,27)=any a.a.
<220> FEATURE:
<221> NAME/KEY: MISC_FEATURE
<222> LOCATION: (30)..(31)
<223> OTHER INFORMATION: Xaa(30)=any a.a.
     Xaa(31)=hydrophobic a.a.
<220> FEATURE:
<221> NAME/KEY: MISC_FEATURE
<222> LOCATION: (33)..(39)
<223> OTHER INFORMATION: Xaa(33,35,37-39)=any a.a.
     Xaa(34,36)=hydrophobic a.a.

```
<220> FEATURE:
<221> NAME/KEY: MISC_FEATURE
<222> LOCATION: (60)..(67)
<223> OTHER INFORMATION: Xaa(60,64-65)=hydrophilic a.a.
      Xaa(61,66)=hydrophobic a.a.
      Xaa(62-63,67)=any a.a.
<220> FEATURE:
<221> NAME/KEY: MISC_FEATURE
<222> LOCATION: (70)..(75)
<223> OTHER INFORMATION: Xaa(70)=hydrophilic a.a.
      Xaa(71-75)=any or no a.a.
<220> FEATURE:
<221> NAME/KEY: MISC_FEATURE
<222> LOCATION: (81)..(81)
<223> OTHER INFORMATION: Xaa=hydrophobic a.a.
<220> FEATURE:
<221> NAME/KEY: MISC_FEATURE
<222> LOCATION: (87)..(87)
<223> OTHER INFORMATION: Xaa=any a.a.
<220> FEATURE:
<221> NAME/KEY: MISC_FEATURE
<222> LOCATION: (95)..(95)
<223> OTHER INFORMATION: Xaa=hydrophilic a.a.
<220> FEATURE:
<221> NAME/KEY: MISC_FEATURE
<222> LOCATION: (108)..(108)
<223> OTHER INFORMATION: Xaa=hydrophilic a.a.
<220> FEATURE:
<221> NAME/KEY: MISC_FEATURE
<222> LOCATION: (127)..(127)
<223> OTHER INFORMATION: Xaa=any a.a.
<220> FEATURE:
<221> NAME/KEY: MISC_FEATURE
<222> LOCATION: (131)..(132)
<223> OTHER INFORMATION: Xaa=hydrophilic a.a.
<220> FEATURE:
<221> NAME/KEY: MISC_FEATURE
<222> LOCATION: (138)..(138)
<223> OTHER INFORMATION: Xaa=any a.a.
<220> FEATURE:
<221> NAME/KEY: MISC_FEATURE
<222> LOCATION: (140)..(142)
<223> OTHER INFORMATION: Xaa=any or no a.a.
<220> FEATURE:
<221> NAME/KEY: MISC_FEATURE
<222> LOCATION: (153)..(153)
<223> OTHER INFORMATION: Xaa=hydrophilic a.a.
<220> FEATURE:
<221> NAME/KEY: MISC_FEATURE
<222> LOCATION: (155)..(155)
<223> OTHER INFORMATION: Xaa=any a.a.
<220> FEATURE:
<221> NAME/KEY: MISC_FEATURE
<222> LOCATION: (168)..(168)
<223> OTHER INFORMATION: Xaa=hydrophobic a.a.
<220> FEATURE:
<221> NAME/KEY: MISC_FEATURE
<222> LOCATION: (185)..(185)
<223> OTHER INFORMATION: Xaa=any a.a.
<220> FEATURE:
<221> NAME/KEY: MISC_FEATURE
<222> LOCATION: (197)..(197)
<223> OTHER INFORMATION: Xaa=any a.a.
<220> FEATURE:
<221> NAME/KEY: MISC_FEATURE
<222> LOCATION: (200)..(200)
<223> OTHER INFORMATION: Xaa=hydrophilic a.a.
<220> FEATURE:
<221> NAME/KEY: MISC_FEATURE
<222> LOCATION: (208)..(208)
<223> OTHER INFORMATION: Xaa=hydrophilic a.a.

<400> SEQUENCE: 3

Met Met Xaa Xaa Xaa Xaa Xaa Phe Ala Xaa Xaa Cys Xaa Ala Xaa Xaa
1               5                   10                  15

Gln Ala Asn Xaa Thr Xaa Asn Xaa Xaa Xaa Xaa Asp Ile Xaa Xaa Val
            20                  25                  30
```

```
Xaa Xaa Xaa Xaa Xaa Xaa Asp Leu Glu Thr Asp Leu Phe Thr Ile
            35                  40                  45

Val Glu Asp Met Asn Val Ile Ser Arg Asp Thr Xaa Xaa Xaa Xaa
 50                  55                  60

Xaa Xaa Xaa Arg Gly Xaa Xaa Xaa Xaa Xaa Leu Pro Gly Lys Lys
 65                  70                  75                  80

Xaa Pro Leu Glu Val Leu Xaa Glu Leu Glu Ala Asn Ala Gln Xaa Ala
                 85                  90                  95

Gly Cys Thr Arg Gly Cys Leu Ile Cys Leu Ser Xaa Ile Lys Cys Thr
                100                 105                 110

Ala Lys Met Lys Lys Trp Leu Pro Gly Arg Cys Glu Ser Trp Xaa Gly
            115                 120                 125

Asp Lys Xaa Xaa Gly Gln Gly Gly Ile Xaa Glu Xaa Xaa Xaa Val Asp
 130                 135                 140

Ile Pro Glu Ile Pro Gly Phe Lys Xaa Leu Xaa Pro Met Glu Gln Phe
 145                 150                 155                 160

Ile Ala Gln Val Asp Leu Cys Xaa Asp Cys Thr Thr Gly Cys Leu Lys
                165                 170                 175

Gly Leu Ala Asn Val Lys Cys Ser Xaa Leu Leu Lys Lys Trp Leu Pro
            180                 185                 190

Ser Arg Cys Ala Xaa Phe Ala Xaa Lys Ile Gln Ala Gln Val Asp Xaa
            195                 200                 205

Ile Lys Gly Ala Gly Gly Ser
            210                 215

<210> SEQ ID NO 4
<211> LENGTH: 209
<212> TYPE: PRT
<213> ORGANISM: Artificial Sequence
<220> FEATURE:
<223> OTHER INFORMATION: Synthetic Sequence

<400> SEQUENCE: 4

Met Met Glu Ile Gln Val Leu Phe Ala Leu Ile Cys Phe Ala Leu Val
  1                   5                  10                  15

Gln Ala Asn Pro Thr Glu Asn Lys Asp Asp Ile Asp Ile Val Gly Val
             20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asn Leu Ala Asn Ser
 50                  55                  60

Asp Ala Asp Arg Gly Lys Leu Pro Gly Lys Lys Leu Pro Leu Glu Val
 65                  70                  75                  80

Leu Lys Glu Leu Glu Ala Asn Ala Gln Lys Ala Gly Cys Thr Arg Gly
                 85                  90                  95

Cys Leu Ile Cys Leu Ser His Ile Lys Cys Thr Ala Lys Met Lys Lys
                100                 105                 110

Trp Leu Pro Gly Arg Cys Glu Ser Trp Glu Gly Asp Lys Glu Thr Gly
            115                 120                 125

Gln Gly Gly Ile Gly Glu Ala Ile Val Asp Ile Pro Glu Ile Pro Gly
 130                 135                 140

Phe Lys Asp Leu Glu Pro Met Glu Gln Phe Ile Ala Gln Val Asp Leu
 145                 150                 155                 160

Cys Val Asp Cys Thr Thr Gly Cys Leu Lys Gly Leu Ala Asn Val Lys
                165                 170                 175
```

```
Cys Ser Asp Leu Leu Lys Lys Trp Leu Pro Ser Arg Cys Ala Thr Phe
            180                 185                 190

Ala Ser Lys Ile Gln Ala Gln Val Asp Lys Ile Lys Gly Ala Gly Gly
        195                 200                 205

Ser

<210> SEQ ID NO 5
<211> LENGTH: 209
<212> TYPE: PRT
<213> ORGANISM: Artificial Sequence
<220> FEATURE:
<223> OTHER INFORMATION: Synthetic Sequence

<400> SEQUENCE: 5

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
50                  55                  60

Arg Ala Asp Arg Gly Lys Leu Pro Gly Lys Lys Leu Pro Leu Glu Val
65                  70                  75                  80

Leu Lys Glu Leu Glu Ala Asn Ala Gln Lys Ala Gly Cys Thr Arg Gly
                85                  90                  95

Cys Leu Ile Cys Leu Ser His Ile Lys Cys Thr Ala Lys Met Lys Lys
            100                 105                 110

Trp Leu Pro Gly Arg Cys Glu Ser Trp Glu Gly Asp Lys Glu Thr Gly
        115                 120                 125

Gln Gly Gly Ile Gly Glu Ala Ile Val Asp Ile Pro Glu Ile Pro Gly
    130                 135                 140

Phe Lys Asp Leu Glu Pro Met Glu Gln Phe Ile Ala Gln Val Asp Leu
145                 150                 155                 160

Cys Val Asp Cys Thr Thr Gly Cys Leu Lys Gly Leu Ala Asn Val Lys
                165                 170                 175

Cys Ser Asp Leu Leu Lys Lys Trp Leu Pro Ser Arg Cys Ala Thr Phe
            180                 185                 190

Ala Ser Lys Ile Gln Ala Gln Val Asp Lys Ile Lys Gly Ala Gly Gly
        195                 200                 205

Ser

<210> SEQ ID NO 6
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 6

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45
```

Val Glu Asp Met Asn Val Ile Ser Arg Asp Thr Asp Val Asp Ala Asn
 50                  55                  60

Arg Ala Asp Arg Gly Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
             85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
            180                 185                 190

Ala Thr Phe Ala Ser Lys Ile Gln Ala Gln Val Asp Lys Ile Lys Gly
        195                 200                 205

Ala Gly Gly Ser
        210

<210> SEQ ID NO 7
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 7

Met Met Gly Ile Lys Val Leu Phe Ala Leu Ile Cys Phe Ala Leu Val
 1               5                  10                  15

Gln Ala Asn Pro Thr Glu Asn Lys Asp Asp Ile Asp Ile Val Gly Val
             20                  25                  30

Glu Gly Lys Phe Gly Thr Thr Asp Leu Glu Thr Asp Leu Phe Thr Ile
         35                  40                  45

Val Glu Asp Met Asn Val Ile Ser Arg Asp Thr Asp Val Asp Ala Asn
 50                  55                  60

Arg Ala Asp Arg Gly Arg Gly Lys Met Pro Gly Lys Lys Leu Pro
 65                  70                  75                  80

Lys Ala Val Leu Ile Glu Leu Glu Ala Asn Ala Gln Lys Ala Gly Cys
             85                  90                  95

His Arg Gly Cys Leu Ile Cys Leu Ser His Ile Lys Cys Thr Ala Lys
            100                 105                 110

Met Lys Glu Trp Leu Pro Gly Arg Cys Glu Ser Trp Gly Gly Asp Lys
        115                 120                 125

Glu Thr Gly Gln Ala Gly Ile Val Gly Ala Ile Val Asp Ile Pro Glu
130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
            180                 185                 190

```
Ala Thr Phe Ala Ser Lys Ile Gln Ala Gln Val Asp Lys Ile Lys Gly
            195                 200                 205

Ala Gly Gly Ser
        210

<210> SEQ ID NO 8
<211> LENGTH: 215
<212> TYPE: PRT
<213> ORGANISM: Artificial Sequence
<220> FEATURE:
<223> OTHER INFORMATION: Synthetic Sequence

<400> SEQUENCE: 8

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly His Gly Gly Leu Pro Gly Lys Lys
65                  70                  75                  80

Met Pro Leu Glu Val Leu Leu Glu Leu Glu Ala Asn Ala Gln Arg Ala
                85                  90                  95

Gly Cys Thr Arg Gly Cys Leu Ile Cys Leu Ser Lys Ile Lys Cys Thr
            100                 105                 110

Ala Lys Met Lys Lys Trp Leu Pro Gly Arg Cys Glu Ser Trp Ala Gly
        115                 120                 125

Asp Lys Glu Thr Gly Gln Gly Gly Ile Thr Glu Glu Thr Val Asp
    130                 135                 140

Ile Pro Glu Ile Pro Gly Phe Lys Asp Leu Glu Pro Met Glu Gln Phe
145                 150                 155                 160

Ile Ala Gln Val Asp Leu Cys Val Asp Cys Thr Thr Gly Cys Leu Lys
                165                 170                 175

Gly Leu Ala Asn Val Lys Cys Ser Asp Leu Leu Lys Lys Trp Leu Pro
            180                 185                 190

Ser Arg Cys Ala Thr Phe Ala Ser Lys Ile Gln Ala Gln Val Asp Lys
        195                 200                 205

Ile Lys Gly Ala Gly Gly Ser
    210                 215

<210> SEQ ID NO 9
<211> LENGTH: 217
<212> TYPE: PRT
<213> ORGANISM: Artificial Sequence
<220> FEATURE:
<223> OTHER INFORMATION: Synthetic Sequence

<400> SEQUENCE: 9

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60
```

```
Arg Ala Asp Arg Gly Arg Gly Arg Lys Leu Pro Gly Lys Lys Leu
 65                  70                  75                  80

Pro Lys Glu Val Leu Lys Ile Leu Glu Ala Asn Ala Gln Arg Ala Gly
                 85                  90                  95

Cys His Arg Gly Cys Leu Ile Cys Leu Ser His Ile Lys Cys Thr Ala
            100                 105                 110

Lys Met Lys Gln Trp Leu Pro Gly Arg Cys Glu Ser Trp Glu Gly Asp
        115                 120                 125

Lys Glu Thr Gly Gln Gly Gly Ile Gly Gly Pro Ile Val Asp Ile Gly
    130                 135                 140

Val Leu Gly Pro Glu Ile Pro Gly Phe Lys Asp Leu Glu Pro Met Glu
145                 150                 155                 160

Gln Phe Ile Ala Gln Val Asp Leu Cys Val Asp Cys Thr Thr Gly Cys
                165                 170                 175

Leu Lys Gly Leu Ala Asn Val Lys Cys Ser Asp Leu Leu Lys Lys Trp
            180                 185                 190

Leu Pro Ser Arg Cys Ala Thr Phe Ala Ser Lys Ile Gln Ala Gln Val
        195                 200                 205

Asp Lys Ile Lys Gly Ala Gly Gly Ser
    210                 215

<210> SEQ ID NO 10
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 10

Met Met Gly Ile Lys Val Leu Phe Ala Leu Ile Cys Phe Ala Leu Val
  1               5                  10                  15

Gln Ala Asn Ala Thr Ile Asn Glu Glu Asp Ile Asp Leu Val Ala Ile
                 20                  25                  30

Gly Gly Ser Phe Ala Thr Thr Asp Leu Glu Thr Asp Leu Phe Thr Ile
            35                  40                  45

Val Glu Asp Met Asn Val Ile Ser Arg Asp Thr Asp Val Asp Ala Asn
 50                  55                  60

Arg Ala Asp Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
            180                 185                 190
```

```
Ala Thr Phe Ala Ser Lys Ile Gln Ala Gln Val Asp Lys Ile Lys Gly
            195                 200                 205

Ala Gly Gly Ser
    210

<210> SEQ ID NO 11
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 11

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
50                  55                  60

Arg Gly Gly Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
            180                 185                 190

Ala Thr Phe Ala Ser Lys Ile Gln Ala Gln Val Asp Lys Ile Lys Gly
        195                 200                 205

Ala Gly Gly Ser
    210

<210> SEQ ID NO 12
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 12

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
50                  55                  60
```

```
Arg Ala Asp Arg Gly Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 13
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 13

Met Met Gly Ile Lys Val Leu Phe Ala Leu Ile Cys Phe Ala Leu Val
 1               5                  10                  15

Gln Ala Asn Pro Thr Glu Asn Lys Asp Asp Ile Asp Ile Val Gly Val
                 20                  25                  30

Glu Gly Lys Phe Gly Thr Thr Asp Leu Glu Thr Asp Leu Phe Thr Ile
             35                  40                  45

Val Glu Asp Met Asn Val Ile Ser Arg Asp Thr Asp Val Asp Ala Asn
 50                  55                  60

Arg Ala Asp Arg Gly Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Asn Met Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Asn Leu Leu Lys Lys Trp Leu Pro Ser Arg Cys
            180                 185                 190
```

```
Lys Gly Phe Ala Asn Lys Ile Gln Ala Glu Val Asp Thr Ile Lys Gly
        195                 200                 205

Leu Gly Gly Ser
    210

<210> SEQ ID NO 14
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 14

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Gly Gly Arg Gly Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 15
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 15

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60
```

Arg Gly Gly Arg Gly Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Asn Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Asn Leu Leu Lys Lys Trp Leu Pro Ser Arg Cys
            180                 185                 190

Ala Gly Phe Ala Asn Lys Ile Gln Ala Gln Val Asp Thr Ile Lys Gly
        195                 200                 205

Leu Gly Gly Ser
    210

<210> SEQ ID NO 16
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 16

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
                20                  25                  30

Ala Ile Gly Gly Ser Phe Ala Asp Leu Glu Thr Asp Leu Phe Thr Ile
            35                  40                  45

Val Glu Asp Met Asn Val Ile Ser Arg Asp Thr Asp Val Asp Ala Asn
50                  55                  60

Arg Gly Gly Arg Gly Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Phe Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Phe Cys Ser Phe Leu Leu Lys Lys Trp Leu Pro Ser Arg Cys
            180                 185                 190

```
Ala Gly Phe Ala Phe Lys Ile Gln Ala Gln Val Asp Thr Ile Lys Gly
            195                 200                 205

Leu Gly Gly Ser
    210

<210> SEQ ID NO 17
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 17

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
                20                  25                  30

Ala Ile Gly Gly Ser Phe Ala Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60

Arg Gly Gly Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Tyr Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Tyr Cys Ser Tyr Leu Leu Lys Lys Trp Leu Pro Ser Arg Cys
            180                 185                 190

Ala Gly Phe Ala Tyr Lys Ile Gln Ala Gln Val Asp Thr Ile Lys Gly
        195                 200                 205

Leu Gly Gly Ser
    210

<210> SEQ ID NO 18
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 18

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
                20                  25                  30

Ala Ile Gly Gly Ser Phe Ala Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60
```

```
Arg Gly Gly Arg Gly Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Trp Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Trp Cys Ser Trp Leu Leu Lys Lys Trp Leu Pro Ser Arg Cys
            180                 185                 190

Ala Gly Phe Ala Trp Lys Ile Gln Ala Gln Val Asp Thr Ile Lys Gly
        195                 200                 205

Leu Gly Gly Ser
    210
```

<210> SEQ ID NO 19
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 19

```
Met Met Gly Ile Lys Val Leu Phe Ala Leu Ile Cys Phe Ala Leu Val
  1               5                  10                  15

Gln Ala Asn His His His His His His His Asp Ile Val Gly Val
                 20                  25                  30

Glu Gly Lys Phe Gly Thr Thr Asp Leu Glu Thr Asp Leu Phe Thr Ile
             35                  40                  45

Val Glu Asp Met Asn Val Ile Ser Arg Asp Thr Asp Val Asp Ala Asn
 50                  55                  60

Arg Ala Asp Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190
```

```
Ala Gly Phe Ala Asp Lys Ile Gln Ala Gln Val Asp Thr Ile Lys Gly
            195                 200                 205

Ala Gly Gly Ser
    210

<210> SEQ ID NO 20
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 20

Met Met Gly Ile Lys Val Leu Phe Ala Leu Ile Cys Phe Ala Leu Val
1               5                   10                  15

Gln Ala Asn His His His His His His His Asp Ile Val Gly Val
            20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60

Arg Ala Asp Arg Gly Arg Gly Glu Leu Pro Gly Lys Lys Leu Pro
65                  70                  75                  80

Leu Glu Val Leu Lys Glu Leu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
            195                 200                 205

Ala Gly Gly Ser
    210

<210> SEQ ID NO 21
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 21

Met Met Gly Ile Lys Val Leu Phe Ala Leu Ile Cys Phe Ala Leu Val
1               5                   10                  15

Gln Ala Asn Glu Gln Lys Leu Ile Ser Glu Glu Asp Leu Val Gly Val
            20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60
```

```
Arg Ala Asp Arg Gly Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 22
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 22

Met Met Gly Ile Lys Val Leu Phe Ala Leu Ile Cys Phe Ala Leu Val
  1               5                  10                  15

Gln Ala Asn Met Met Tyr Pro Tyr Asp Val Pro Asp Tyr Ala Gly Val
                 20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
 50                  55                  60

Arg Ala Asp Arg Gly Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190
```

Ala Gly Phe Ala Asp Lys Ile Gln Ala Gln Val Asp Thr Ile Lys Gly
            195                 200                 205

Ala Gly Gly Ser
    210

<210> SEQ ID NO 23
<211> LENGTH: 212
<212> TYPE: PRT
<213> ORGANISM: Artificial Sequence
<220> FEATURE:
<223> OTHER INFORMATION: Synthetic Sequence

<400> SEQUENCE: 23

Met Met Gly Ile Lys Val Leu Phe Ala Leu Ile Cys Phe Ala Leu Val
1               5                   10                  15

Gln Ala Asn Met Met Asp Tyr Lys Asp Asp Asp Lys Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Gly Lys Leu Pro Gly Lys Lys Leu Pro
65                  70                  75                  80

Leu Glu Val Leu Lys Glu Leu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 24
<211> LENGTH: 69
<212> TYPE: PRT
<213> ORGANISM: Artificial Sequence
<220> FEATURE:
<223> OTHER INFORMATION: Synthetic Sequence

<400> SEQUENCE: 24

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
        50                  55                  60

Arg Ala Asp Arg Gly
 65

<210> SEQ ID NO 25
<211> LENGTH: 149
<212> TYPE: PRT
<213> ORGANISM: Artificial Sequence
<220> FEATURE:
<223> OTHER INFORMATION: Synthetic Sequence

<400> SEQUENCE: 25

Met Met Gly Val Lys Leu Ile Phe Ala Val Leu Cys Val Ala Val Ala
 1               5                   10                  15

Gln Ala Asn Ala Thr Ile Asn Glu Asn Phe Glu Asp Ile Asp Leu Val
                20                  25                  30

Ala Ile Gly Gly Ser Phe Ala Asp Leu Glu Thr Asp Leu Phe Thr Ile
            35                  40                  45

Val Glu Asp Met Asn Val Ile Ser Arg Asp Thr Asp Val Asp Ala Asn
        50                  55                  60

Arg Gly Gly Arg Gly Arg Arg Gly Lys Leu Pro Gly Lys Lys Leu Pro
 65                 70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys
145

<210> SEQ ID NO 26
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 26

Pro Thr Glu Asn Lys Asp Asp Ile
 1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 27

Ala Thr Ile Asn Glu Glu Asp Ile
 1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic Sequence

```
<400> SEQUENCE: 28

Ala Thr Ile Asn Glu Asn Phe Glu
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 29

His His His His His His His His
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 30

Glu Lys Leu Ile Ser Glu Glu
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 31

Met Met Tyr Pro Tyr Asp Val Pro
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 32

Met Met Asp Tyr Lys Asp Asp Asp
1               5

<210> SEQ ID NO 33
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 33

Ile Gly Glu Ala
1

<210> SEQ ID NO 34
<211> LENGTH: 4
<212> TYPE: PRT
<213> ORGANISM: Artificial Sequence
<220> FEATURE:
<223> OTHER INFORMATION: Synthetic Sequence
```

```
<400> SEQUENCE: 34

Ile Val Gly Ala
1

<210> SEQ ID NO 35
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 35

Ile Thr Glu Glu Glu
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 36

Ile Gly Gly Pro Ile Val Asp
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 37

Pro Thr Glu Asn Lys Asp Asp Ile
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 38

Ala Thr Ile Asn Glu Glu Asp Ile
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 39

Ala Thr Ile Asn Glu Asn Phe Glu Asp Ile
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic Sequence
```

```
<400> SEQUENCE: 40

His His His His His His His
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 41

Glu Lys Leu Ile Ser Glu Glu
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 42

Met Met Tyr Pro Tyr Asp Val Pro
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 43

Met Met Asp Tyr Lys Asp Asp Asp
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 44

Thr Glu Glu Glu Thr
1               5

<210> SEQ ID NO 45
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 45

Gly Glu Ala Ile
1

<210> SEQ ID NO 46
<211> LENGTH: 4
<212> TYPE: PRT
<213> ORGANISM: Artificial Sequence
<220> FEATURE:
<223> OTHER INFORMATION: Synthetic Sequence
```

```
<400> SEQUENCE: 46

Val Gly Ala Ile
1

<210> SEQ ID NO 47
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 47

Gly Val Leu Gly
1

<210> SEQ ID NO 48
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 48

His His His His His His
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 49

Asp Tyr Lys Asp Asp Asp Asp Lys
1               5

<210> SEQ ID NO 50
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 50

Glu Gln Lys Leu Ile Ser Glu Glu Asp Leu
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 51

Tyr Pro Tyr Asp Val Pro Asp Tyr Ala
1               5

<210> SEQ ID NO 52
<211> LENGTH: 11
<212> TYPE: PRT
<213> ORGANISM: Artificial Sequence
<220> FEATURE:
<223> OTHER INFORMATION: Synthetic Sequence
```

```
<400> SEQUENCE: 52

Met Leu Cys Cys Met Arg Arg Thr Lys Gln Val
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 53

Gly Arg Lys Lys Arg Gln Arg Arg Arg
1               5                   10

<210> SEQ ID NO 54
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 54

Lys Asp Glu Leu
1

<210> SEQ ID NO 55
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 55

Asp Pro Lys Lys Lys Arg Lys Val
1               5

<210> SEQ ID NO 56
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 56

Gly Lys Pro Ile Pro Asn Pro Leu Leu Gly Leu Asp Ser Thr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 57

Met Ala Ser Met Thr Gly Gly Gln Gln Met Gly
1               5                   10

<210> SEQ ID NO 58
<211> LENGTH: 648
<212> TYPE: DNA
<213> ORGANISM: Artificial Sequence
<220> FEATURE:
<223> OTHER INFORMATION: Synthetic Sequence
```

```
<400> SEQUENCE: 58
atgatgggta taaaggttct ttttgctctc atttgctttg cattggtgca ggccaatccc      60
actgagaata aggacgacat cgacatcgtt ggagtcgaag gcaagtttgg gaccactgat     120
ctggaaacag acctgttcac catcgttgag gatatgaacg tgatttcccg agacacggac     180
gtcgatgcca acagagcaga tcggggacga cgaggtcatg gtgggcttcc agggaagaag    240
atgcccttgg aagtgctgct ggaactggag gcaaacgctc agagggctgg atgcactcgc    300
ggatgcctga tctgcttgtc caagatcaaa tgcacggcga aaatgaagaa gtggcttcct    360
ggccgctgtg agagttgggc tggagataag gagacagggc aaggcggcat aaccgaggaa    420
gagactgtcg acatacccga gatacccggc ttcaaggatc tggaaccgat ggagcagttc    480
attgcccagg ttgacctttg cgttgactgt accacaggtt gcctgaaagg ccttgctaac    540
gtcaagtgca gtgatctcct gaagaagtgg cttccaagta ggtgtgctac gtttgccagc    600
aagatccagg cccaggtcga caagatcaag ggagctggcg ggtcgtga                 648
```

LUMINESCENT SUBSTRATE FOR USE IN ARTIFICIAL BIOLUMINESCENT ENZYME

CROSS REFERENCE TO RELATED APPLICATIONS

This patent application is the U.S. national phase of International Patent Application No. PCT/JP2014/077618, filed Oct. 16, 2014, which the benefit of Japanese Patent Application No. 2013-217560, filed on Oct. 18, 2013, the disclosure of which is incorporated herein by reference in its entirety.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 61,199 bytes ASCII (Text) file named "724013-ReplacementSequenceListing.txt," created Jun. 8, 2016.

TECHNICAL FIELD

The present invention relates to a bioluminescent substrate suitably usable in artificial bioluminescent enzymes (ALuc) created based on the common genetic information of marine animal-derived bioluminescent enzymes. Specifically, the invention relates to a substrate necessary for inducing high-intensity luminescence characteristics and luminescence sustainability, which are advantageous to ALuc, and particularly relates to the design and development of efficient luminescent substrates based on the steric structure of ALuc.

BACKGROUND ART

The establishment of many novel bioluminescent enzymes (luciferases) has recently been reported. For example, Promega reported the establishment of a novel bioluminescent enzyme originating from a deep-sea shrimp (Non-patent Literature 1). The molecular weight of this enzyme is half (19 kD) that of a known *Renilla* luciferase (RLuc), and its luminescence intensity is a 100-fold increase. Further, Shigeri et al. reported 11 types of plankton-derived bioluminescent enzyme (Non-patent Literature 20). Some of these bioluminescent enzymes were evaluated as having a luminescence intensity comparable to that of RLuc.

Further, some deep-sea luminescent animals belonging to the Augaptiloidea superfamily have heretofore been discovered (Non-patent Literature 2). In addition, a bioluminescent enzyme originating from *Gaussia princeps* (GLuc), a bioluminescent enzyme originating from *Metridia longa* (MLuc), and bioluminescent enzymes originating from *Metridia pacifica* (MpLuc1 and MpLuc2), which all belong to the Metridinidae family, have also been discovered (Non-patent Literature 15, 19, and 21).

Moreover, InvivoGen has recently established an artificial bioluminescent enzyme, "Lucia," which is similar to the bioluminescent enzymes originated from copepods (http://www.invivogen.com/lucia).

Meanwhile, research for improving the luminescence intensity or luminescence stability of these bioluminescent enzymes has progressed. Loening et al. established stable RLuc variants having high luminescence intensity by using a method of introducing amino acid mutations into RLuc (Non-patent Literature 14). In their study, a "consensus sequence-driven mutagenesis strategy" was used to specify the mutation introduction site (Non-patent Literature 13). Further, the present inventors also succeeded in improving the luminescence intensity and luminescence stability of GLuc, MpLuc1, and MLuc, which are bioluminescent enzymes originating from deep-sea luminescent animals, by using a method of predicting the enzyme active site based on a hydrophilic amino acid distribution chart, and introducing a variant into the site (Non-patent Literature 11).

The present inventors previously suggested production of a thermodynamically stable bioluminescent enzyme sequence from an attempt to obtain information regarding the luminescence characteristics by bisecting a single bioluminescent enzyme sequence, and aligning the first half and the second half of the sequence based on the homology of amino acids (single sequence alignment; SSA) (Non-patent Literature 3). This method is based on the premise that a marine animal-derived bioluminescent enzyme has two enzyme active sites. By aligning the two split-enzyme active sites based on amino acid similarity, it is possible to easily examine the similarity between the former half and the rear half of the active site. This method attempts to produce a thermodynamically stable bioluminescent enzyme sequence by increasing the similarity of the former and rear half of the sequence on the aforementioned presumption that the amino acid frequency is relevant to the thermodynamic stability (Patent Application No. 2012-237043).

Meanwhile, various applied technologies using a bioluminescent enzyme as a "reporter" have also been developed. Niu et al. classified the bioassays using a bioluminescent enzyme as a reporter into three groups: "basic," "inducible," and "activatable" (Non-patent Literature 16). This classification is based on the characteristics of the reporter gene. First of all, the difference between "basic" and "inducible" is the presence or absence of an expression controlling character in the reporter expression by the promoter, and the difference in expression amount. A later-described antibody having a bioluminescent enzyme attached thereto corresponds to "basic," and the bioluminescence resonance energy transfer (BRET) and two-hybrid assay belong to the category of "inducible." The reporter-gene probes, which belong to the category of "activatable," are characterized in that the reporter actively responds to ligand stimulation and produces bioluminescence. The later-described protein complementation assay (PCA), protein splicing assay (PSA), integrated-molecule-format bioluminescent probe, bioluminescent capsule, and the like belong to the category of "activatable."

For the bioassays (hereinafter may also be simply referred to as "reporter assays") using these bioluminescent enzymes as a reporter, various bioluminescent probes have been actively developed based on the aforementioned novel bioluminescent enzymes. The present inventors have heretofore conducted research and development regarding bioluminescence imaging using unique molecular design technology. More specifically, the inventors developed a method of measuring translocation of transcription factors into the nucleus or nongenomic protein-protein interactions in the cytosol using protein splicing (Non-patent Literature 7 and 8), and an integrated-molecule-format bioluminescent probe in which all of the necessary elements for signal recognition and bioluminescence emission are integrated (Non-patent Literature 4 and 6). Thereafter, the probes were multicolorized, and developed to be capable of simultaneous imaging of multiple signal-transduction processes (Non-patent Literature 12). Moreover, the inventors further developed a circular permutation technique (Non-patent Literature 9) and a molecular design technology using low-molecular-weight bioluminescent enzymes (Non-patent Literature 12) as strategies for improving the ligand sensitivity of the bioluminescent probe. These technologies have been used as means for efficiently measuring molecular phenomena in cellular and cell-free systems.

Regarding the main research tools for exploring intra- or extracellular molecular phenomena, fluorescence imaging has been used more widely than luminescence imaging. However, due to their autofluorescence property, fluorescent proteins generate a high background, requiring an external light source. Therefore, fluorescence imaging requires a large instrumentation, such as a fluorescence microscope, and a sophisticated light-filtering system. Fluorescence imaging also has a drawback in that the maturation of a fluorescence chromophore takes at least several hours to several days. Further, since the number of simultaneously observable cells is limited for each measurement with a fluorescence microscope, quantitative measurement has been problematic (Non-patent Literature 8).

On the other hand, bioluminescence imaging using a bioluminescent enzyme has, despite its many advantages, a critical problem regarding poor luminescence intensity of bioluminescent enzymes. This problem has decreased the popular use of bioluminescence imaging, compared with fluorescence imaging. Because of this poor bioluminescence intensity of bioluminescent enzymes, high-sensitivity detectors were required; therefore, bioluminescent enzymes have been considered inappropriate for single-cell imaging or exploration of organelles.

Further, studies on multicolor fluorescent proteins have greatly progressed, and many facts regarding their coloring mechanisms have been discovered; thus, many fluorescent proteins with diversified fluorescent characters have been developed based on these study results.

In contrast, only limited kinds of bioluminescent enzymes allow multiple colors. Although it has been known that the diversification of bioluminescent colors is advantageous in that (i) it enables the simultaneous measurement of multiple cellular signals, and that (ii) it ensures a tissue permeability of red-shifted bioluminescence in living subjects, nearly no systematic study for diversifying the colors of bioluminescent enzymes based on their luminescence mechanisms has been conducted.

In addition, appropriate selection of the reaction solution is an important factor in bioassays, and may influence the assay results. In particular, (1) reporter-gene assay, (2) two-hybrid assay, (3) enzyme-linked immunosorbent assay, and (4) radioimmunoassay (RIA) (Non-patent Literature 22 and Non-patent Literature 23) require more careful selection of the reaction solution.

Recently, the present inventors developed a multiple recognition-type bioluminescent probe, which is fabricated by combination of reporter-gene assay and integrated-molecule-format bioluminescent probe (Non-patent Literature 27). This probe is characterized by two sensing steps for a single target substance. The present inventors further developed a multicolor bioluminescence imaging probe set by combining two integrated-molecule-format bioluminescent probes with distinctive colors (Patent Literature 5). This probe set is characterized by multicolor imaging of multiple aspects of bioactivity of a test substance.

Bioassays require a reaction solution, which may be roughly classified into (1) a method using a fluorescent protein and (2) a method using a bioluminescent enzyme (luciferase), depending on the type of the luminescence signal. In the method using a fluorescent protein, a high background is generated due to the autofluorescence, and an external light source is necessary. Further, a relatively large luminescence detector having a precise spectral filter is problematically necessary to measure the fluorescence (e.g., a fluorescence microscope) (Non-patent Literature 8). On the other hand, although the method using a bioluminescent enzyme does not have the above problems, it indispensably requires substrates because of a drawback such that the light emission of bioluminescence is weaker than that of fluorescence. Further, since the method using a bioluminescent enzyme relies on the luminescence of enzyme, easy changes in luminescence quantity depending on the salt concentration, temperature, pH, heavy-metal ion concentration, and the like become problematic. The method using fluorescence also has similar problems. Therefore, to fix the pH and optimize the luminescence reaction conditions, reaction solutions are widely used both in the fluorescence method and the luminescence method.

To improve the assay effect, various additives have been used for reaction solutions (assay buffer). The additives must have functions for ensuring homogenous assay conditions, including (1) prevention of protein decomposition by protease, (2) suppression of influences of interfering substances, (3) ensuring the function as a buffer solution for supporting stable signal generation, and (4) allowing mild lysis of the plasma membrane. Therefore, the additives (5) must stabilize the protein and (6) must not inhibit the probe performance that is the core of the luminescence reaction.

The major additives of the reaction solution include, as salts, NaCl, KCl, $(NH_4)_2SO_4$, and the like; as an SH reagent, mercaptoethanol, DTT, and the like; as a polyol, glycerol, sucrose, and the like; and as a chelating reagent, EGTA, EDTA, and the like.

Examples of surfactants include polyoxyethylene (10) octylphenyl ether (Triton X-100; TX100), Nonidet P-40 (NP40), polyoxyethylene sorbitan monolaurate (Tween 20; TW20), polyoxyethylene sorbitan monooleate (Tween 80; TW80), polyoxyethylene (20) cetyl ether (Brij58), sodium dodecyl sulfate (SDS), and the like. Heretofore, a suitable surfactant has been selected by referring to the order of the hydrophilic degree of the surfactants, which is TW20>Brij58>TW80>TX100>NP40, and the order of the degree of surface activity, which is NP40>TX100>Brij58>TW20>TW80.

Examples of protease inhibitors to be used for inhibiting protein decomposition include aprotinin (molecular weight: 6.5 kD), leupeptin (molecular weight: 427), pepstatin A (molecular weight: 686), phenylmethylsulfonyl fluoride (PMSF, molecular weight: 174), antipain (molecular weight: 605), chymostatin (molecular weight: 608) and the like. Further, Pefabloc SC (AEBSF, 240 Da), DFP (184 Da), p-APMSF (216 Da), STI (20,100 Da), leupeptin (460 Da), N-tosyl-L-phenylalaninechloromethylketone, 3,4-dichloroisocoumarin (215 Da), EDTA-Na2 (372 Da), EGTA (380 Da), 1,10-phenanthroline (198 Da), phosphoramidon (580 Da), Dithiobis (2-amino-4-methylpentane), E-64 (357 Da), cystatin, bestatin, epibestatin hydrochloride, aprotinin, minocycline, ALLN (384 Da), and the like have been used as protein decomposition inhibitors.

Further, the functional chemical substances below may also be added. By adding sodium molybdate, it is possible to stabilize the receptors and thus protect them from decomposition. Glycerol can be used as a protein preserving agent. Dithiothreitol (DTT) has been used as a reducing agent.

Additionally, as buffers, p-toluenesulfonic acid, tartaric acid, citric acid, phthalate, glycine, trans-aconitic acid, formic acid, 3,3-dimethylglutaric acid, phenylacetic acid, sodium acetate, succinic acid, sodium cacodylate, sodium hydrogen maleate, maleic acid, sodium phosphate, $KH_2PO_4$, imidazole, 2,4,6-trimethylpyridine, triethanolamine hydrochloride, sodium 5,5-diethylbarbiturate, N-ethylmorpholine, sodium pyrophosphate, tris(hydroxymethyl)aminomethane, bicine, 2-amino-2-methylpropane-1,3-diol, diethanolamine, potassium p-phenolsulfonate, boric acid, sodium borate, ammonia, glycine, $Na_2CO_3/NaHCO_3$, sodium borate, or a combination of these substances, have been used.

As described above, the trend of the previous studies has been directed toward the establishment of novel high-intensity bioluminescent enzymes and the enhancement of luminescence stability, heat resistance, or salt resistance. The establishment of bioluminescent enzymes with a red-shifted luminescence spectrum has also attracted attention in recent studies. Not only the establishment of bioluminescent enzymes but also the optimization of the reaction solutions is expected to contribute to improving the stability of luminescence signals, luminescence intensity, and signal-to-noise ratio (S/N ratio). To achieve the object, attempts to optimally prepare various additives (e.g., preservatives, surfactants, and protease inhibitors) have been made.

A substrate, another factor that enables luminescence intensity, luminescence stability, and red-shifted luminescence, finds its basis in studies several decades ago, and the technical progress remains far too slow. The reason for this slow progress is that (1) because studies on luminescent substrates essentially involve organic synthesis, only a limited group of researchers capable of performing organic synthesis have been engaged in studies in this field; and (2) because, among bioluminescent enzymes, marine animal-derived bioluminescent enzymes are particularly susceptible to oxidation in the air, the synthetic environment must be well prepared.

The definition of a substrate is not precisely established and has been changed over time. Luciferin was initially defined as a substance indispensable for the luminescent reaction and an extract from a luminescent organ of animals. In around 1960, the luciferin of Cypridina was discovered from bioluminescent fish parapriacanthus, and during 1790 to 1980, coelenterazine was discovered. Such luciferins were isolated from a variety of luminescent animals and identified as a substrate for many marine animal-derived bioluminescent enzymes (Non-patent Literature 5).

The present invention focuses on coelenterazine as a substrate usable for the luminescent reaction of artificial bioluminescent enzymes and unveils the chemical structure and reaction mechanism of a substrate optimum to artificial bioluminescent enzymes. Coelenterazine was first isolated from *Renilla reniformis* in the mid-1960s. In 1977, the chemical structure was elucidated by efforts of Inoue et al. (Non-patent Literature 10). Shimomura (2008 Nobel laureate in chemistry) named the substance as coelenterazine in 1975.

Subsequent studies based on these findings on coelenterazine made by the foregoing researchers led to the synthesis of more than 50 coelenterazine derivatives (Non-patent Literature 30 and 31). Coelenterazine derivatives have been studied for more than the past three decades and reported in many non-patent documents. Coelenterazine and its derivatives are thus considered no longer patentable, and recent patent applications in this field are more focused on the development of novel synthesis routes (Patent Literature 6).

Traditionally, coelenterazine and its derivatives have been synthesized through the following synthesis route (Non-patent Literature 17, 18, 24, 26, 28, and 29).

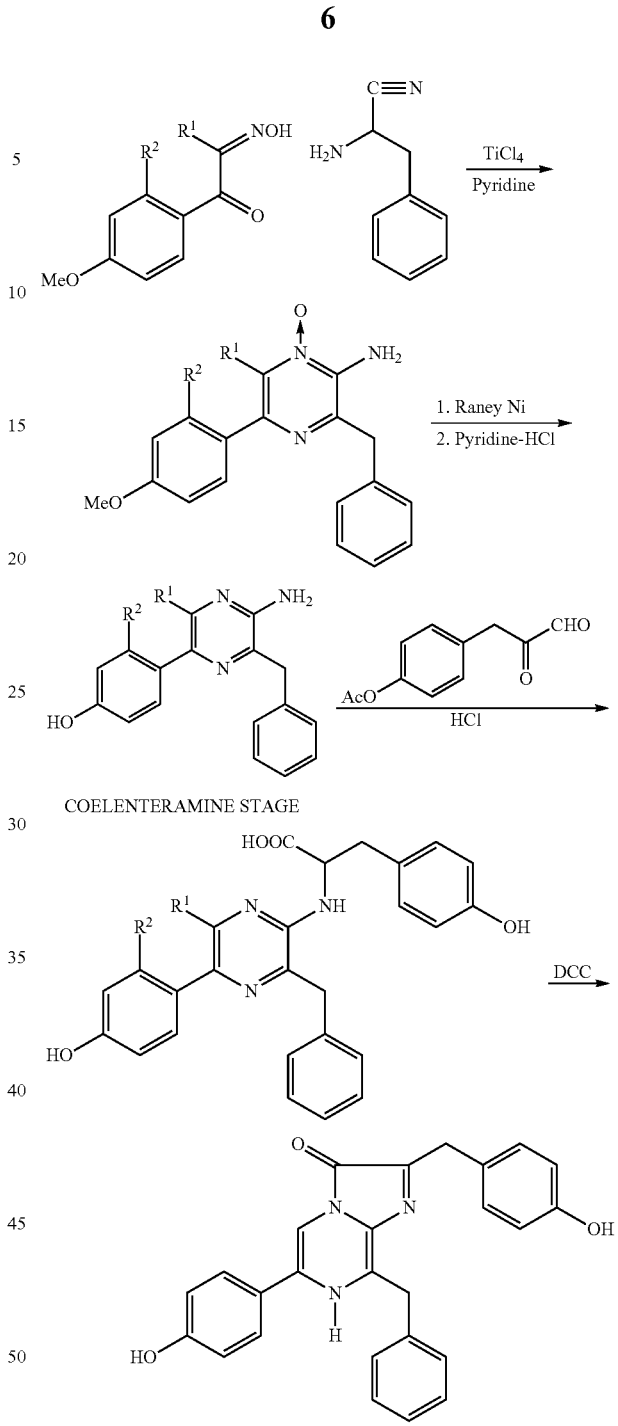

COELENTERAMINE STAGE

Palladium-catalyzed cross coupling (Stille coupling) was established in relatively recent years as a simpler coelenteramine synthesis technique. The synthesis route follows the procedure described below (Non-patent Literature 32, 33, and 34).

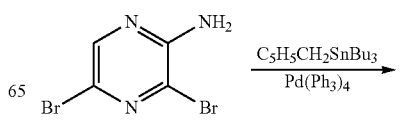

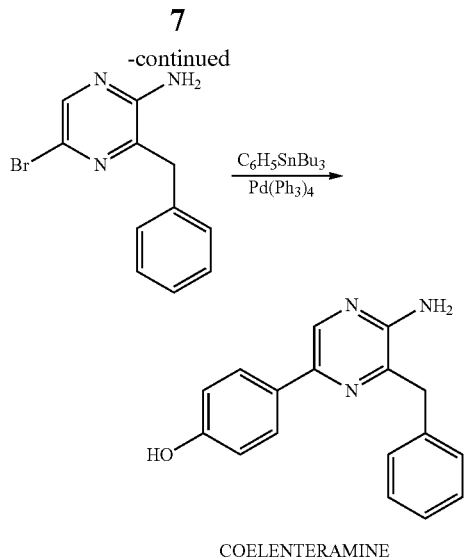

COELENTERAMINE

Although many coelenterazine derivatives have been synthesized over the past decades in accordance with the basic synthesis technique, most of the synthesized derivatives have rarely been used because of the unsatisfactory luminescence intensity and luminescence stability. Despite the difficulties involved in the derivative synthesis, native coelenterazine has still been widely used. In addition, not many studies have been made on efficient substrates suitable for bioluminescent enzymes, which is also another reason why this field remains relatively unexplored.

Accordingly, there has been urgent demand for search for efficient substrates that are suitable for bioluminescent enzymes and that have overcome the conventional luminescence intensity and stability problems.

CITATION LIST

Patent Literature

Patent Literature 1: U.S. Pat. No. 8,124,424
Patent Literature 2: U.S. Pat. No. 8,043,827
Patent Literature 3: U.S. Patent Publication No. US2009-0269781 (A1)
Patent Literature 4: WO2008/084869 (international application No. PCT/JP2008/050370)
Patent Literature 5: JP2009-034059A
Patent Literature 6: WO2010/090319 (laid-open disclosure date: Aug. 12, 2010)
Patent Literature 7: WO2014/065047 (international application No. PCT/JP2013/075202)

Non-Patent Literature

Non-patent Literature 1: Hall, M. P., Unch, J., Binkowski, B. F., et al. ACS Chem. Biol. 7 2012 1848.
Non-patent Literature 2: Herring, P. J., Latz, M. I., Bannister, N. J., et al. Marine Ecology-Progress Series, 94 1993 297.
Non-patent Literature 3: Kim, S. B. Protein Engineering Design & Selection, 25 2012 261.
Non-patent Literature 4: Kim, S. B., Awais, M., Sato, M., et al. Anal. Chem., 79 2007 1874.
Non-patent Literature 5: Osamu Shimomura "bioluminescence" Book, World Scientific (Singapore), 2006.
Non-patent Literature 6: Kim, S. B., Otani, Y., Umezawa, Y., et al. Anal. Chem., 79 2007 4820.
Non-patent Literature 7: Kim, S. B., Ozawa, T., Umezawa, Y. Anal. Chem., 77 2005 6588.
Non-patent Literature 8: Kim, S. B., Ozawa, T., Watanabe, S., et al. Proc. Natl. Acad. Sci. U.S.A., 101 2004 11542.
Non-patent Literature 9: Kim, S. B., Sato, M., Tao, H. Bioconjugate Chem., 19 2008 2480.
Non-patent Literature 10: Inoue et al. Tetrahedron Lett. 1977 31 2685.
Non-patent Literature 11: Kim, S. B., Suzuki, H., Sato, M., et al. Anal. Chem., 83 2011 8732.
Non-patent Literature 12: Kim, S. B., Umezawa, Y., Kanno, K. A., et al. ACS Chem. Biol. 3 2008 359.
Non-patent Literature 13: Lehmann, M., Loch, C., Middendorf, A., et al. Protein Eng., 14 2002 403.
Non-patent Literature 14: Loening, A. M., Wu, A. M., Gambhir, S. S. Nat. Methods, 4 2007 641.
Non-patent Literature 15: Markova, S. V., Golz, S., Frank, L. A., et al. J. Biol. Chem., 279 2004 3212.
Non-patent Literature 16: Niu, G., Chen, X. Y. Theranostics, 2 2012 413.
Non-patent Literature 17: Kishi et al. Tetrahedron Lett. 1972, 27, 2747.
Non-patent Literature 18: Inoue et al. Chem Lett 1975, 141.
Non-patent Literature 19: Takenaka, Y., Masuda, H., Yamaguchi, A., et al. Gene, 425 2008 28.
Non-patent Literature 20: Takenaka, Y., Yamaguchi, A., Tsuruoka, N., et al. Molecular Biology and Evolution, 29 2012 1669.
Non-patent Literature 21: Verhaegent, M., Christopoulos, T. K. Anal. Chem., 74 2002 4378.
Non-patent Literature 22: S. B. Kim, H. Tao, and Y. Umezawa eds., "Cellular and Biomolecular Recognition", edited by R. Jelinek, p. 299 ((2009) (Wiley-VCH, Darmstadt)).
Non-patent Literature 23: W. Li and N. B. Caberoy, Applied Microbiology and Biotechnology 85 (4), 909 (2010).
Non-patent Literature 24: Shimomura et al. Photochem Photohiol 1989, 49, 355.
Non-patent Literature 25: S. W. Michnick, P. H. Ear, C. Landry et al., Meth. Enzymol. 470, 335 (2010).
Non-patent Literature 26: Teranishi et al. Bull Chem Soc Japan 1990, 63, 3132.
Non-patent Literature 27: S. B. Kim, Y. Takenaka, and M. Torimura, Bioconjugate Chem. 22 (9), 1835 (2011).
Non-patent Literature 28: Teranishi et al. K Bull Chem Soc Japan 1990, 63, 3132.
Non-patent Literature 29: Teranishi et al. K Anal Biochem 1997, 249, 37.
Non-patent Literature 30: Shimomura et al. Biochem J, 1988, 251, 405.
Non-patent Literature 31: Inouye et al. Biochem Biophys Res Comm, 2008, 365, 96.
Non-patent Literature 32: Nakamura et al. Synlett 1995, 12 1227.
Non-patent Literature 33: Wu et al. Tetrahedron Lett 2001, 42, 2997.
Non-patent Literature 34: Jones et al. Synlett 1996, 6 509.
Non-patent Literature 35: Izumi et al. J. Chem. Inf. Model., 2013, 53 (3), 584.
Non-patent Literature 36: Okita et al. Nature, 2007, 448, 313.

SUMMARY OF INVENTION

Technical Problem

The present invention is intended to show novel findings on an optimum luminescent substrate for the artificial bioluminescent enzyme (ALuc) disclosed in the previous patent application by closely examining the amino acid sequence of ALuc and conducting architectural analysis of the steric structure of ALuc.

Solution to Problem

To find out an optimum luminescent substrate for the artificial bioluminescent enzyme (ALuc) developed by the present inventors, they speculated the supersecondary structure of ALuc employing all of the findings on bioluminescent enzymes they have acquired and conducted research on the chemical structure of bioluminescent substrate that suitably match the steric structure of ALuc.

Among all bioluminescent enzymes, marine animal-derived bioluminescent enzymes, in particular, have high sequence similarity each other and have common characteristics in that luminescence is caused by the same or similar substrate (coelenterazine). The present inventors previously found a method for specifying an enzyme active site by using a hydrophilicity search (Non-patent Literature 11). This method can be used to roughly speculate the enzyme active site but not to pinpoint which amino acid is important.

To examine the bioluminescent enzyme sequence information in more detail, a novel bioluminescent enzyme sequence, which does not occur in nature, was created in accordance with the following procedure. First, the inventors aligned marine animal bioluminescent enzyme sequences in a public database (NCBI) based on the amino acid similarity, and extracted frequently occurring amino acids based on an individualistic approach. With this method, the inventors produced many artificial luciferase (ALuc) sequences that did not exist in the past.

Further, the inventors once reported that a single bioluminescent enzyme has two enzyme active sites (Non-patent Literature 3). The inventors trisected the amino acid sequences of all of the copepod-derived bioluminescent enzymes obtained from the NCBI at an arbitrary portion. After aligning all the former and rear sequences, the inventors compared corresponding amino acids in the amino acid sequences, and determined an amino acid sequence so that the similarity increases. In this manner, the inventors determined many amino acid sequences as candidates of novel artificial bioluminescent enzymes (Patent Literature 7).

By examining the sequence characteristics of the artificially produced N-terminus using PSORTII, the localization can be predicted in silico. By using such bioinformatics software provided by public database for predicting the sequence behavior, the inventors increased the probability of sequence efficiency.

The study enabled the actual production of artificial bioluminescent enzymes, providing sufficient supersecondary structure information of the enzymes. However, this study alone cannot provide findings on an optimum substrate. Thus, the steric structure of the artificial bioluminescent enzymes was created based on the supersecondary structure information of the enzymes to thereby determine the optimum substrate based on the steric structure in accordance with the following procedure (FIG. 2).

X-ray crystallographic data (PDBID: 2hpsA, 2hq8A) of coelenterazine-binding protein (CBP) were converted to corresponding conformation codes, the following three forms, α-helix (h), β-sheet (s), and other (o), in terms of the conformation of the main chain of each amino acid residue by using the method described in a prior art document (Non-patent Literature 35). Then, the supersecondary structure was described.

Further, CBP and ALuc30 were compared with respect to the homology of their amino acid sequence and found to have a homology of 16.7%. Amino acid sequences were aligned on the basis of the homology, and amino acid residues in the structural data of 2hpsA were substituted using MolFeat v4.5 (http://www.fiatlux.co.jp/product/life-science/molfeat/mol-index.html) to thereby prepare a molecular model. Then, insertion and deletion of amino acid residues were performed along the alignment using Hyper-Protein v1.0 (http://www.hyper.com/Products/HyperProtein/tabId/504/Default.aspx) and Chem3D Ultra v8.0 (http://www.cambridgesoft.com/Ensemble_for_Chemistry/ChemBio3D) to have a supersecondary structure match, thereby cautiously performing molecular modeling including coelenterazine. Lastly, molecular mechanics (MM) calculation was performed by using the Polak-Ribiere algorithm to optimize the structure.

The steric structure of ALuc30 was found to be made in the form of a molecular model maintaining the main supersecondary structure of CBP including the loop structure, for example. An analysis on the amino acids near 4 Å distance from the hydroxy group of the hydroxybenzyl residue and the hydroxy group of the hydroxyphenyl residue of native coelenterazine (coelenterazine) revealed that, for example, 17LYS, 20THR, 37ILE, 72ASN, 143VAL, 145LEU, 149CYS, 189LYS, and 192GLY are expected to have a particularly large impact on bioluminescence. The His tag adjacent to positions 20 to 30 is located at an α-helix portion forming a rigid supersecondary structure, and thus, neighboring amino acid residues may adversely influence the original function of the His tag.

An analysis was conducted on the three-dimensional positional information (i.e., steric structure) of amino acids constituting ALuc30 as an example of artificial bioluminescent enzymes. FIG. 1B shows a model obtained by the analysis.

The detailed examination of the chemical structure of coelenterazine and its derivatives (hereinafter, "coelenterazines") described below led to the discovery of coelenterazines specifically reactive to an artificial bioluminescent enzyme (FIG. 1). As shown in FIG. 1, coelenterazine has an imidazole frame structure with three residues. The residues have the following characteristics and individually interact with an artificial bioluminescent enzyme.

(I) As seen in the steric structure of the artificial bioluminescent enzyme shown in FIG. 2, residue A (R-A) of coelenterazine is located at the innermost part of the bioluminescent enzyme, and a large space is present around R-A. This space shows the acceptable volume of the functional group to be bound to R-A. Based on the findings, several coelenterazine derivatives, particularly those having a large functional group bound to R-A, were selected from dozens of known coelenterazine derivatives, and the luminescence intensity was studied (FIG. 3).

(II) As seen in the steric structure shown in FIG. 2, amino acids (e.g., Phe at position 157, Lys at position 149, Gly at position 136, Glu at position 137, and Gly at position 133) are present near residue B (R-B) of coelenterazine. This suggests that a residue capable of causing π-π stacking such as a benzene ring or hydrophobic interaction is preferable at the R-B site. In view of the findings, verification experiments were conducted on dozens of known coelenterazine derivatives by dividing them into groups, one having a benzene-ring structure at R-B and the other not having a benzene-ring structure at R-B (FIG. 3).

(III) As seen in the steric structure shown in FIG. 2, residue C (R-C) interacts particularly with an amino acid located near the end of the amino acid sequence of a bioluminescent enzyme. For example, residue C (R-C) is known to interact with amino acids, such as Leu at position 165, Cys at position 169, Lys at position 209, and Gly at position 212. Because these amino acids may be located at the terminus of artificial bioluminescent enzymes, the amino acids appear to form a flexible structure and to also be in the relatively hydrophilic environment. To suit such an environment, R—C is required to have a certain level of hydrophilicity. This suggests that it is ideal for R-C to have a hydrophilic functional group (e.g., hydroxy) in its benzene-ring structure. In view of the findings, comparative experiments were conducted using, among known coelenterazine derivatives, a derivative having no functional group binding to the benzene ring of R-C (i.e., coelenterazine 400A) (FIG. 3).

As described above, detailed examination based on the steric structure of an artificial bioluminescent enzyme elucidated the chemical structure of an ideal luminescent substrate, and led to the completion of the present invention.

Specifically, the present invention encompasses the following aspects.

Item 1

Use of a compound as a luminescent substrate for a polypeptide comprising an amino acid sequence (i) or (ii) below, and having a copepod luciferase activity:
(i) the amino acid sequence of SEQ ID No: 1; and
(ii) the amino acid sequence of SEQ ID No: 1 in which one or more amino acids are deleted in at least one of a region corresponding to positions 1-31 and a region corresponding to positions 217-221, wherein the compound is represented by the following formula (1)

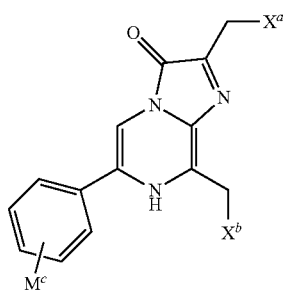

wherein $X^a$ represents a phenyl group optionally substituted with halogen or naphthyl,
$X^b$ represents a phenyl group, and
$M^c$ represents hydrogen, hydroxy, or thiol groups.

Item 2

The use according to Item 1, wherein the compound represented by formula (1) is coelenterazine n (CTZ n), coelenterazine i (CTZ i), coelenterazine f (CTZ f), coelenterazine h (CTZ h), or coelenterazine 400A (CTZ 400A).

Item 3

A bioluminescence assay comprising the steps of
contacting the following compound (A) with the following polypeptide (B), and
measuring intensity of luminescence generated by the contact,
wherein compound (A) is represented by the following formula (1)

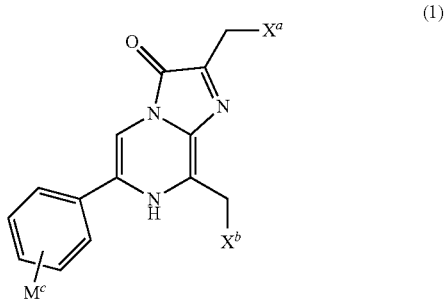

wherein $X^a$ represents a phenyl group optionally substituted with halogen or naphthyl,
$X^b$ represents a phenyl group, and
$M^c$ represents hydroxy or thiol, and
wherein polypeptide groups (B) comprises an amino acid sequence (i) or (ii) below and has a copepod luciferase activity:
(i) the amino acid sequence of SEQ ID No: 1; and
(ii) the amino acid sequence of SEQ ID No: 1 in which one or more amino acids are deleted in at least one of a region corresponding to positions 1-31 and a region corresponding to positions 217-221.

Item 4

A kit for measuring bioluminescence for use in the bioluminescence assay according to Item 3, the kit comprising a compound represented by formula (1)

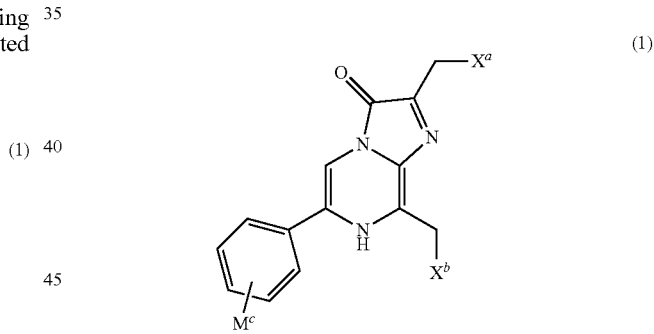

wherein $X^a$ represents a phenyl group optionally substituted with halogen or naphthyl,
$X^b$ represents a phenyl group, and
$M^c$ represents hydrogen, hydroxy, or thiol groups.

Item 5

A multicolor imaging method comprising conducting the assay according to Item 3 using the polypeptide in combination with one or more different bioluminescent enzymes, and measuring two or more bioluminescent colors.

Item 6

The assay according to Item 3, which is a reporter gene assay, a two-hybrid assay, a bioluminescent capsule assay, or an integrated-molecule-format bioluminescent probe measurement method.

Item 7

A bioluminescence resonance energy transfer (BRET) method comprising the steps of
contacting the following compound (A) with the following polypeptide (B), allowing luminescent energy generated by the contact to transfer to another fluorescence protein, and measuring luminescence intensity of the fluorescence protein to which the luminescent energy has transferred, wherein compound (A) is represented by the following formula (1)

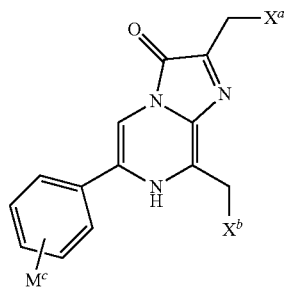

wherein $X^a$ represents a phenyl group optionally substituted with halogen or naphthyl, $X^b$ represents a phenyl group, and $M^c$ represents hydrogen, hydroxy, or thiol, and wherein polypeptide groups (B) comprises an amino acid sequence (i) or (ii) below and has a copepod luciferase activity:

(i) the amino acid sequence of SEQ ID No: 1; and (ii) the amino acid sequence of SEQ ID No: 1 in which one or more amino acids are deleted in at least one of a region corresponding to positions 1-31 and a region corresponding to positions 217-221.

Advantageous Effects of Invention

The present invention relates to the development of an optimum luminescent substrate for an artificial bioluminescent enzyme (ALuc), which was previously developed by the present inventors, and does not occur in nature. To achieve the object, the inventors unveiled the steric structure of ALuc (in particular, the substrate-biding site and important amino acids), and gained insight into the chemical structure of the substrate that suitably matches the steric structure of ALuc. The inventors further studied the luminescent characteristics of many coelenterazine derivatives in line with the findings, and elucidated an optimum luminescent substrate for ALuc.

As shown in FIG. 3, coelenterazine derivatives (e.g., CTZ n, CTZ i, CTZ f, and CTZ i), which were selected to have a controlled R-A size in the Examples of the specification, exhibited selectivity (intensity standard) to ALuc 100 to 10,000 times higher than their selectivity to *Renilla* luciferase 8.6-535 (RLuc-8.6-535; a representative of known luciferases).

The use of such a substrate having a high substrate-selectivity to ALuc enables the development of a variety of bioassay systems. For example, since CTZ i, only with ALuc, exhibits high luminescence intensity, combining CTZ i with RLuc8.6-535 enables the creation of multicolor imaging systems (including a dual assay system). For example, three kinds of bioluminescent enzymes of different color (ALuc, RLuc8.6-535, and CLuc) are expressed in the same cultured cells. First, the enzymes are allowed to produce luminescence in the presence of a luminescent substrate used exclusively for ALuc (e.g., CTZ i) and the luminescence is quenched. Second, the enzymes are allowed to produce luminescence in the presence of a substrate specific to RLuc8.6-535, and the bioluminescent enzyme is deactivated (quenched) by SDS. Lastly, the enzymes are allowed to produce luminescence in the presence of a substrate used exclusively for CLuc. CLuc, which is vigorous due to an abundance of Cys, is not deactivated by SDS, thereby providing such assay system. For this system, of course, a suitable filter can be attached to a photodetector, taking advantage of different colors of the bioluminescent enzymes to thereby prevent crosstalk between signals.

In bioassay systems using a different ALuc as well, the use of a substrate having specificity to the ALuc can achieve an unprecedented specific luminescent reaction, multicolor characteristics, and high precision attributable to the absence of crosstalk between luminescence signals. Examples of conventional bioassays that can use this technique include a reporter gene assay, a yeast two-hybrid assay, a mammalian two-hybrid assay, a protein splicing assay (PSA), a protein complementation assay (PCA), a circular permutation assay, a bioluminescence resonance energy transfer (BRET) assay, and a bioluminescent capsule method.

A bioassay improved in performance by the present invention has a potential of enhanced usefulness, when combined with the optimum reaction solution for bioassays previously invented by the present inventors (JP2014-085311A, Japanese Patent Application No. 2012-236872). For example, the use of the optimum reaction solution (one-shot buffer) in the assay described above is expected to suppress the background light, increase the signal intensity, and enhance the luminescence intensity. Further, the simplified and shortened experiment procedure can save time and work, thereby improving the S/N ratio and reproducibility, while reducing costs in the bioassay.

BRIEF DESCRIPTION OF DRAWINGS

FIG. 6A An example of a sequence of the artificial bioluminescent enzyme of the present invention; the amino acid sequence represented by SEQ ID NO: 3. In the figure, "x" represents any amino acid. The lower case "y" represents a hydrophobic amino acid. "z" represents a hydrophilic amino acid.

FIG. 6B An example of a sequence of the artificial bioluminescent enzyme of the present invention. "ALucCM" denotes the amino acid sequence represented by SEQ ID NO: 2. In the figure, "x" represents any amino acid (or blank). "o" represents a hydrophobic amino acid, "j" represents a hydrophilic amino acid, "." represents a low-molecular-weight aliphatic amino acid, "@" represents a high-molecular-weight aliphatic amino acid, "+" represents a positively charged amino acid, and "−" represents a negatively charged amino acid.

FIG. 6C An example of a sequence of the artificial bioluminescent enzyme of the present invention. "ALucCM" denotes an amino acid sequence represented by SEQ ID NO: 1. In the figure, "x" represents any amino acid (or blank). "○" represents a hydrophobic amino acid, "j" represents a hydrophilic amino acid, "." represents a low-molecular-weight aliphatic amino acid, "@" represents a high-molecular-weight aliphatic amino acid, "+" represents a positively charged amino acid, and "−" represents a negatively charged amino acid.

DESCRIPTION OF EMBODIMENTS

Figure 1:
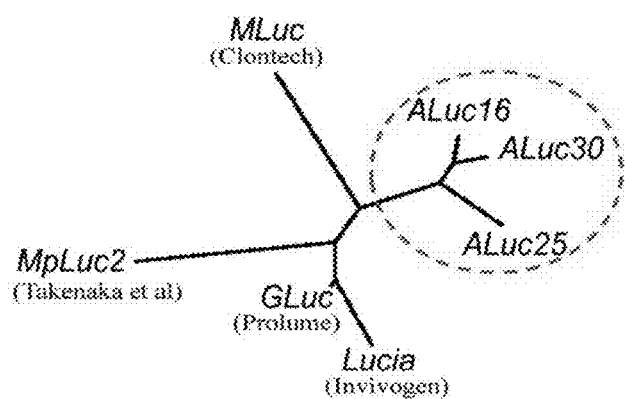
FIG. 1 The phylogenetic characteristics and steric structure of an artificial bioluminescent enzyme (ALuc). (A) Study on the phylogenetic correlation between a commercially available copepod bioluminescent enzyme and ALuc. The dotted line shows artificial bioluminescent enzymes developed by the present inventors. (B) The supersecondary steric structure of ALuc30. The chemical structure is of a substrate (coelenterazine). R-A, R-B, and R—C each represent a residue of the luminescent substrate. H1 to H9 each represent a helix number.
Figure 1:
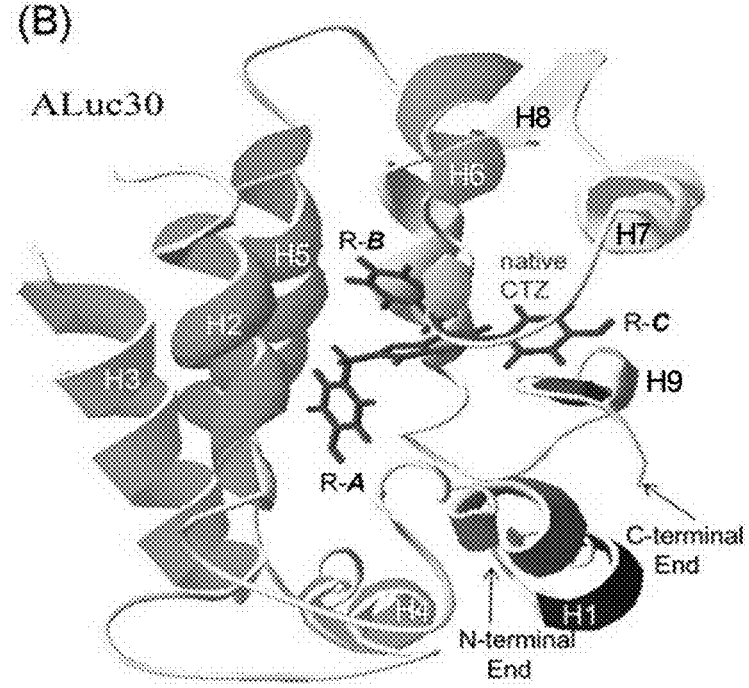

[I] Artificial bioLuminescent Enzyme and Luminescent Substrate
1. Optimum Luminescent Substrate for Artificial bioLuminescent Enzymes (ALuc)
Luminescent Substrate
The luminescent substrate of the present invention is a compound represented by the following formula (1).

wherein $X^a$ represents a phenyl group optionally substituted with one halogen atom or naphthyl group (naphthalene). The position of the substituent (ortho-, meta-, or para-) is not limited. However, when the phenyl group has a substituent, the position is preferably meta- or para-, and particularly preferably para-.

As used herein, the halogen atom refers to chlorine, bromine, fluorine, or iodine.

$X^b$ represents a phenyl group.

$M^c$ represents one hydrogen atom, hydroxyl group, or thiol group. The position of hydroxy or thiol groups on the benzene ring (ortho-, meta-, or para-) is not limited, but is preferably meta- or para-, and particularly preferably para-.

Examples of the compound of the present invention include typically coelenterazine n (CTZ n), coelenterazine i (CTZ i), coelenterazine f (CTZ f), coelenterazine h (CTZ h), and coelenterazine 400A (CTZ 400A). Although CTZ n, CTZ i, CTZ f, and CTZ h are particularly preferable, the compound is not limited thereto.

The following shows the chemical structural formulae of coelenterazine n (CTZ n), coelenterazine i (CTZ i), coelenterazine f (CTZ f), coelenterazine h (CTZ h), and coelenterazine 400A (CTZ 400A).

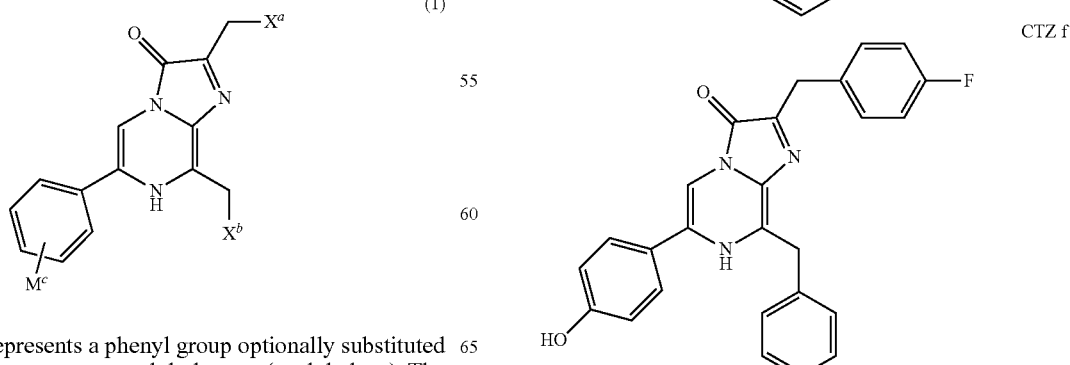

-continued

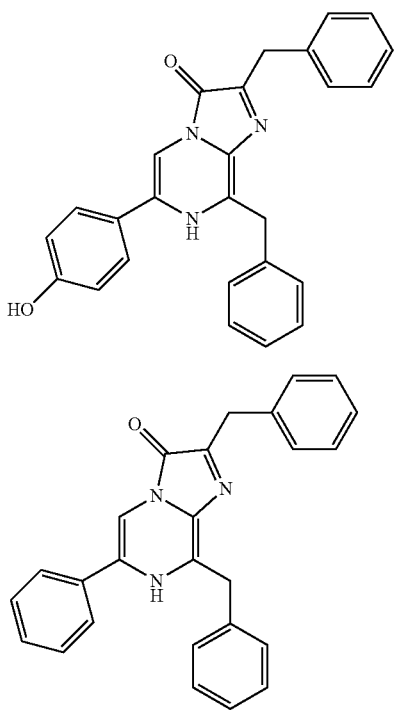

CTZ h

CTZ 400A

The luminescent substrate of the present invention can be synthesized by, for example, following a synthesis route disclosed in Non-patent Literature 17, 18, 24, 26, 28, or 29.

The luminescent substrate can also be synthesized by cross coupling (Stille coupling) catalyzed by palladium as disclosed in Non-patent Literature 32, 33, or 34.

Artificial bioLuminescent Enzyme

In the present invention, the luminescent substrates are used for the following artificial bioluminescent enzymes (which may be referred to sometimes as "artificial luciferase" or "ALuc").

Examples of typical artificial luciferases (ALuc) of the present invention include ALuc10 (SEQ ID NO: 4), ALuc15 (SEQ ID NO: 5), ALuc16 (SEQ ID NO: 6), ALuc17 (SEQ ID NO: 7), ALuc18 (SEQ ID NO: 8), ALuc19 (SEQ ID NO: 9), ALuc21 (SEQ ID NO: 10), ALuc22 (SEQ ID NO: 11), ALuc23 (SEQ ID NO: 12), Luc24 (SEQ ID NO: 13), ALuc25 (SEQ ID NO: 14), ALuc26 (SEQ ID NO: 15), ALuc27 (SEQ ID NO: 16), ALuc28 (SEQ ID NO: 17), ALuc29 (SEQ ID NO: 18), ALuc30 (SEQ ID NO: 19), ALuc31 (SEQ ID NO: 20), ALuc32 (SEQ ID NO: 21), ALuc33 (SEQ ID NO: 22), and ALuc34 (SEQ ID NO: 23).

The artificial luciferase (ALuc) of the present invention can be expressed as a polypeptide comprising an amino acid sequence of any one of Items (i) to (iii) below and having copepod luciferase activity:
(i) an amino acid sequence represented by any of SEQ ID NOs: 4 to 23;
(ii) an amino acid sequence represented by any of SEQ ID NOs: 4 to 23 in which one or several amino acids are deleted, substituted, inserted, or added,
in which "several" means 1 to 20, preferably 1 to 10, more preferably 1 to 5 amino acids);
(iii) an amino acid sequence having an identity of not less than 90% with any of amino acid sequences represented by SEQ ID NOs: 4 to 23.

For example, an amino acid sequence having an identity of not less than 95%, not less than 96%, not less than 97%, not less than 98%, not less than 99%, and not less than 99.5% is more preferable.

Figure 6A:
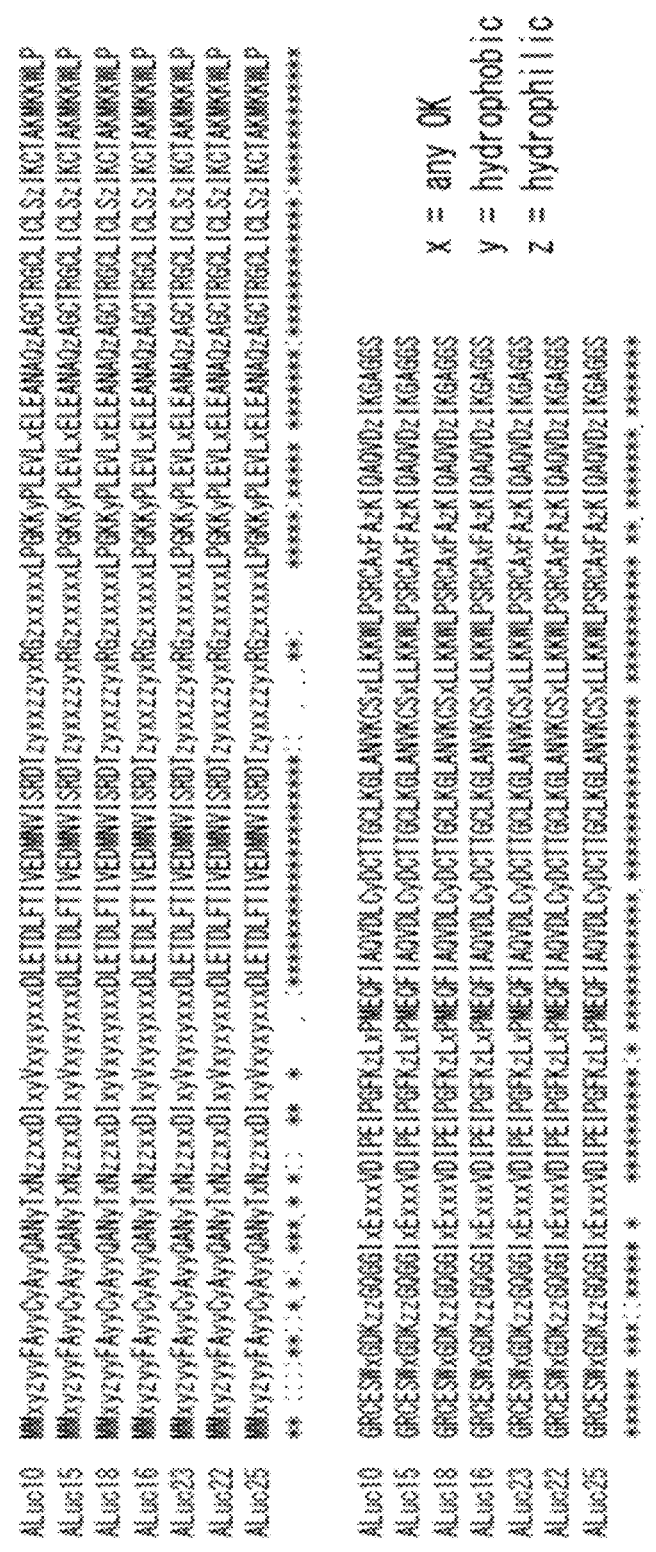
Figure 6B:
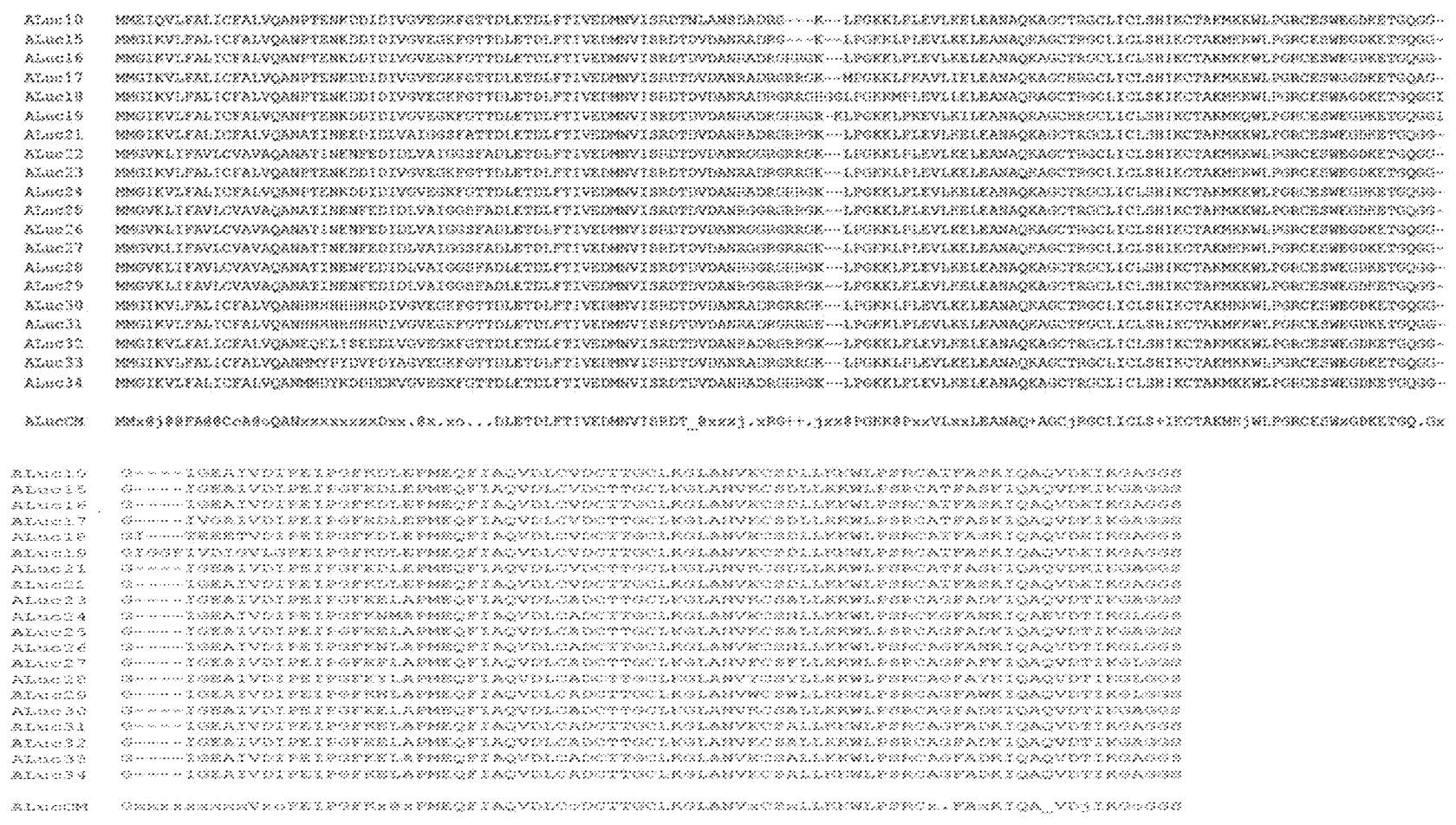
Figure 6C:
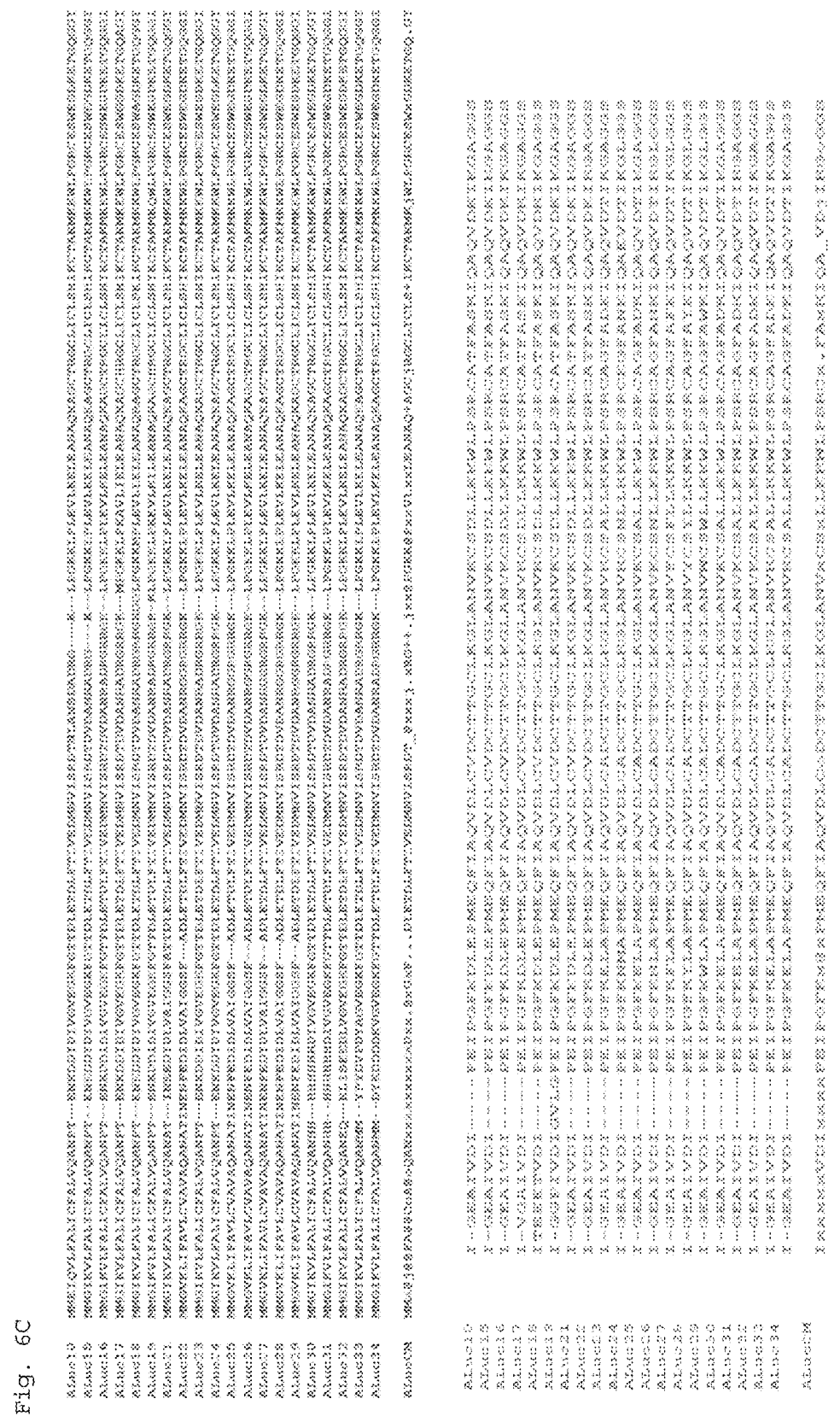

The amino acid sequences of the artificial luciferases (ALucs) of the present invention have common basic frame structures shown in FIGS. 6A to 6C. As long as the artificial luciferases have such a basic frame structure, the luciferases show an equivalent high performance copepod luciferase activity even when amino acids at other positions are freely selected amino acids. Accordingly, the artificial luciferase (ALuc) of the present invention can be expressed as a polypeptide comprising an amino acid sequence of any one of Items (iv) to (vii) below and having copepod luciferase activity:
(iv) the amino acid sequence represented by SEQ ID NO: 2;
(v) an amino acid sequence represented by SEQ ID NO: 2 in which one or more amino acids are deleted in at least one of a region corresponding to positions 1-29 and a region corresponding to positions 214-218;
(iv) the amino acid sequence represented by SEQ ID NO: 1;
(v) an amino acid sequence represented by SEQ ID NO: 1 in which one or more amino acids are deleted in at least one of a region corresponding to positions 1-31 and a region corresponding to positions 217-221;
(vi) the amino acid sequence represented by SEQ ID NO: 3; or
(vii) an amino acid sequence represented by SEQ ID NO: 3 in which one or more amino acids are deleted in at least one of a region corresponding to positions 1-29 and a region corresponding to positions 211-215.

In the amino acid sequence represented by SEQ ID NO: 3, amino acids from positions 1-20 of the N-terminal side are secretion signals (secretion peptide; SP), and a peptide at positions 211-215 of the C-terminal side is a Glycine rich linker peptide (commonly known as a GS linker). Accordingly, part or all of the amino acids in these regions may be deleted. The same applies to positions 1-20 of the N-terminal side and positions 214 to 218 of the C-terminal side in the amino acid sequence represented by SEQ ID NO: 2, and positions 1-20 of the N-terminal side and positions 217-221 of the C-terminal side in the amino acid sequence represented by SEQ ID NO: 1. In copepod luciferases such as *Metridia pacifica* luciferase 1 (MpLuc1) and *Pleuromamma* luciferase, the secretion signals correspond to amino acids at positions 1-18 in *Metridia pacifica* luciferase 1 (MpLuc1), and correspond to amino acids at positions 1-19 in *Pleuromamma* luciferase. It is known that these amino acids may be excluded.

The function of artificial bioluminescent enzyme is not significantly impaired even when the region of positions 20 to 29 in the amino acid sequence represented by SEQ ID NO: 3 (corresponding to a region of positions 20-29 in the amino acid sequence represented by SEQ ID No. 2, and a region of positions 20-31 in the amino acid sequence represented by SEQ ID NO: 1) is substituted with a functional amino acid sequence (e.g., antigen recognition site, affinity chromatography recognition site, or localization signal). Accordingly, part or all of the amino acids in this region may be deleted.

In the amino acid sequences represented by SEQ ID NOs: 1 to 3, amino acids represented by Xaa are explained in detail below.

Of the amino acids represented by Xaa in SEQ ID NO: 2, amino acids at positions 3, 20-27, 29, 30, 33, 35, 62-64, 67, 74, 75, 83, 84, 87, 88, 127, 137-145, 147, 156, 158, 185, 188, 199, and 203 may be any amino acids. Of these, amino acids at positions 74-75 and 137-140 may be deleted. Preferably, position is E or G; positions 20-27 are PTENKDDI (SEQ ID NO: 26), ATINEEDI (SEQ ID NO: 27), ATINENFE (SEQ ID NO: 28), HHHHHHHH (SEQ ID NO: 29), EKLISEE (SEQ ID NO: 30), MMYPYDVP (SEQ ID NO: 31), or MMDYKDDD (SEQ ID NO: 32); position 29 is I, L, Y, or K; position 30 is V, D, or A; position 33 is E, G, or A; position 35 is K, S, or G; positions 62-64 are ANS or DAN; position 67 is D or G, positions 75-76 are GG or K (deletion of one residue), or may be deleted; positions 83-84 are LE, KA, or KE; positions 87-88 are KE, IE, LE, or KI; position 127 is E, G, or A; positions 137-145 are IGEA (deletion of four residues, SEQ ID NO: 33), IVGA (deletion of four residues, SEQ ID NO: 34), ITEEE (deletion of three residues, SEQ ID NO: 35), or IGGPIVD (SEQ ID NO: 36); position 147 is D or L; position 156 is D, E, N, F, Y, or W; position 158 is E or L; position 185 is K, F, Y, or W; position 188 is D, A, N, F, Y, or W; position 199 is A or K; and position 203 is S, D, N, F, Y, or W.

Amino acids at positions 13, 16, 36, 148, 171, and 215 are hydrophobic amino acids (for example, V, F, A, or L), and it is preferable that position 13 is V or F; position 16 is V or A; position 36 is F or G; position 148 is I or G; position 168 is V or A; and position 215 is A or L.

Amino acids at positions 5, 65, 73, 99, 117, and 211 are hydrophilic amino acids (for example, Q, K, D, R, H, E, or T), and it is preferable that position 5 is Q or K; position 65 is D or R; position 73 is K, H, R, or E; position 99 is T or H; position 117 is K, E, or Q; and position 211 is K or T.

Amino acids at positions 4, 6, 7, 10, 11, 15, 31, 32, 37-39, 61, 66, 72, 76, 81, 136, 157, and 200 are aliphatic amino acids, and it is preferable that positions 4, 6, 7, 10, 11, 15, 32, 61, 76, 81, and 157 are high molecular weight aliphatic amino acids (e.g., I, V, L, or M), and more preferably, position 4 is I or V; position 6 is V or L; and position 7 is L or I; position 10 is L or V; position 11 is I or L; position 15 is L or V; position 32 is I or V; position 61 is L or V; position 76 is L or M; position 81 is L or M; and position 157 is L or M. It is also preferable that positions 31, 34, 37-39, 66, 72, 136, and 200 are low molecular weight aliphatic amino acids (e.g., A, G, T, or L), and more preferably, position 31 is G, L, or A; position 34 is G or I; position 37 is G, A, S, or F; position 38 is T or F; position 39 is T or A; position 66 is A or G; position 72 is G or may be deleted; position 136 is G or A; and position 200 is T or G.

Amino acids at positions 70, 71, 95, and 108 are positively-charged amino acids (basic amino acids such as K, R or H), and it is preferable that positions 70 and 71 are each R, or may be deleted; position 95 is K or R; and position 108 is H or K.

Amino acids at positions 60 and 208 are negatively-charged amino acids (acidic amino acids such as N, D, Q, or E), and it is preferable that position 60 is N or D, and position 208 is Q or E.

Of the amino acids represented by Xaa in SEQ ID No. 1, amino acids at positions 3, 20-29, 31, 32, 35, 37, 64-66, 69, 76-77, 85-86, 89-90, 129, 140-144, 148-151, 159, 161, 188, 191, 202, and 206 may be any amino acids. Of these, amino acids at positions 22-23, 39-40, 76-77, 140, and 148-151 may be deleted. Preferably, position 3 is E or G; positions 20-29 are PTENKDDI (deletion of two residues, SEQ ID NO: 37), ATINEEDI (deletion of two residues, SEQ ID NO: 38), ATINENFEDI (SEQ ID NO: 39), HHHHHHHH (deletion of two residues, SEQ ID NO: 40), EKLISEE (deletion of two residues, SEQ ID NO: 41), MMYPYDVP (deletion of two residues, SEQ ID NO: 42), or MMDYKDDD (deletion of two residues, SEQ ID NO: 43); position 31 is I, L, Y, or K; position 32 is V or A; position 35 is E or G; position 37 is K or S; positions 64-66 are ANS or DAN; position 69 is D or G; positions 76-77 are GG or K (deletion of one residue), or may be deleted; positions 85-86 are LE, KA, or KE; positions 89-90 are KE, IE, LE, or KI; position 129 is E, G, or A; positions 140-144 are TEEET (SEQ ID NO: 44), GEAI (deletion of one residue, SEQ ID No. 45), or VGAI (deletion of one residue, SEQ ID NO: 46); positions 148-151 are GVLG (SEQ ID NO: 47) or I (deletion of three residues), or all may be deleted; position 159 is D, E, N, F, Y, or W; position 161 is E or L; position 188 is K, F, Y, or W; position 191 is D, A, N, F, Y, or W; position 202 is A or K; and position 206 is S, D, N, F, Y, or W.

Amino acids at positions 13, 16, 174, and 218 are hydrophobic amino acids (e.g., V, F, A, or L), and it is preferable that position 13 is V or F; position 16 is V or A; position 174 is V or A; and position 218 is A or L.

Amino acids at positions 5, 67, 75, 101, 119, and 214 are hydrophilic amino acids (e.g., Q, K, D, R, H, E, or T), and it is preferable that position 5 is Q or K; position 67 is D or R; position 75 is K, H, R, or E; position 101 is T or H; position 119 is K, E, or Q; and position 211 is K or T.

Amino acids at positions 4, 6, 7, 10, 11, 15, 33, 34, 39-41, 63, 68, 77, 78, 83, 138, 160, and 203 are aliphatic amino acids, and amino acids at positions 39, 40, and 70 may be deleted. It is preferable that positions 4, 6, 7, 10, 11, 15, 34, 63, 78, 83, and 160 are high molecular weight aliphatic amino acids (e.g., I, V, L, or M); however, they may be less-frequently occurring low molecular weight aliphatic amino acids. More preferably, position 4 is I or V; position 6 is V or L; position 7 is L or I; position 10 is L or V; position 11 is I or L; position 15 is L or V; position 34 is I or V; position 63 is L or V; position 78 is L or M; position 83 is L or M; and position 160 is L or M. It is also preferable that positions 33, 39-41, 68, 74, 137, and 203 are low molecular weight aliphatic amino acids (e.g., A, G, or T); however, they may be less-frequently occurring high molecular weight aliphatic amino acids. More preferably, position 33 is G, L, or A; position 39 is G, A, S, or F, or may be deleted; position 40 is T or may be deleted; position 41 is T or A; position 68 is A or G; position 74 is G or may be deleted; position 137 is G or A; and position 203 is T or G.

Amino acids at positions 72, 73, 97, and 110 are positively-charged amino acids (basic amino acids such as K, R or H), and amino acids at positions 72 and 73 may be deleted. It is preferable that positions 72 and 73 are each R, or may be deleted; position 97 is K or R; and position 110 is H or K.

Amino acids at positions 62 and 211 are negatively-charged amino acids (acidic amino acids such as N, D, Q, or E), and it is preferable that position 62 is N or D, and position 211 is Q or E.

Of the amino acids represented by Xaa in SEQ ID NO: 3, amino acids at positions 3, 22, 26, 27, 30, 33, 35, 37-39, 62, 63, 67, 71-75, 87, 127, 138, 140-142, 155, 185, and 197 may be any amino acids. Of these, part or all of the amino acids at positions 71-75 and 140-142 may be deleted. Of hydrophilic amino acids, it is preferable that positions 3, 22, 27, 33, 127, 140, 141, and 155 are E; positions 26, 30, 62, 67, and 185 are D; positions 35 and 87 are K; position 37 is S; positions 38, 39, 138, 142, and 197 are T; position 63 is N; position 71 is R; and position 73 is D or H. Of hydrophobic amino acids, it is preferable that positions 3, 37, 67, 72, 74, 75, 138, and 197 are G; positions 22, 27, and 141 are I; position 30 is V; positions 33, 39, 62, 63, 127, 140, 155, and 185 are A; position 87 is L; and positions 26 and 38 are F.

Amino acids at positions 4, 6, 7, 10, 11, 13, 15, 16, 20, 31, 34, 36, 61, 66, 81, and 168 are hydrophobic amino acids, and it is preferable that position 4 is I or V; position 6 is V or L; position 7 is I or L; position 10 is V or L; position 11 is I or L; and position 13 is V or F; position 15 is V or L; position 16 is V or A; position 20 is A or P; position 31 is L or G; position 34 is I or G; position 36 is F or G; position 61 is V or L; position 66 is A or G; position 81 is L or M; and position 168 is V or A.

Amino acids at positions 5, 24, 25, 60, 64, 65, 70, 95, 108, 153, 200, and 208 are hydrophilic amino acids, and it is preferable that position 5 is Q or K; position 24 is K or E; position 25 is D or N; position 60 is D or N; position 64 is N or S; position 65 is D or R; position 70 is K or R; position 95 is K or R; position 108 is K or H; position 153 is E or D; position 200 is D or S; and position 208 is K, H, or T.

Typical examples of the amino acid sequence represented by SEQ ID NO: 3 include ALuc10, ALuc15, ALuc16, ALuc18, ALuc22, ALuc23, and ALuc25.

One embodiment of the artificial luciferase of the present invention includes the amino acid sequence represented by SEQ ID NO: 24 as the region corresponding to positions 1-71 in the amino acid sequence represented by SEQ ID NO: 1 (corresponding to the region of positions 1-69 in the amino acid sequence represented by SEQ ID NO: 2, and the region of positions 1-69 in the amino acid sequence represented by SEQ ID NO: 3). Typical examples include ALuc15, ALuc16, ALuc17, ALuc18, and ALuc24.

Another embodiment of the artificial luciferase of the present invention includes the amino acid sequence represented by SEQ ID NO: 25 as the region corresponding to positions 1-157 in the amino acid sequence represented by SEQ ID NO: 1 (corresponding to the region of positions 1-155 in the amino acid sequence represented by SEQ ID NO: 2, and the region of positions 1-152 in the amino acid sequence represented by SEQ ID NO: 3). Typical examples include ALuc22, ALuc25, ALuc26, ALuc27, ALuc28, and ALuc29.

Still another embodiment of the artificial luciferase of the present invention includes an antibody recognition site (epitope sequence) therein. "Antibody recognition site" or "epitope sequence" can also be referred to as "antigen site." Typical examples include ALuc30, ALuc31, ALuc32, and ALuc34.

Specifically, in the artificial luciferase embedding an antibody recognition site (epitope sequence) therein, a region corresponding to positions 20-29 in SEQ ID NO: 2 or a region corresponding to positions 20-31 in SEQ ID NO: 1 includes an antibody recognition site (epitope sequence). Preferable examples of the antibody recognition site (epitope sequence) include His-tag (HHHHHH) (SEQ ID NO: 48), FLAG-tag (DYKDDDDK) (SEQ ID NO: 49), Myc-tag (EQKLISEEDL) (SEQ ID NO: 50), and HA-tag (YPYDVPDYA) (SEQ ID NO: 51); however, the antibody recognition site is not limited thereto.

In an example of the artificial luciferase embedding a His-tag therein, amino acids at positions 20-29 in SEQ ID NO: 2 or amino acids at positions 20-31 in SEQ ID NO: 1 are all H (His×8 sequence). Typical examples include ALuc30 and ALuc31.

In an example of the artificial luciferase embedding a c-Myc-tag therein, the sequence of the region corresponding to positions 20-29 in SEQ ID NO: 2 or the sequence of the region corresponding to positions 20 to 31 in SEQ ID NO: 1 is EQKLISEEDL (Myc-tag sequence, SEQ ID NO: 50). Typical examples include ALuc32.

In an example of the artificial luciferase embedding an HA-tag therein, amino acids at positions 20-29 in SEQ ID NO: 2 or amino acids at positions 20-31 in SEQ ID NO: 1 are YPYDVPDYA (HA-tag sequence, SEQ ID NO: 51). Typical examples include ALuc33.

In an example of the artificial luciferase embedding a FLAG-tag therein, amino acids at positions 20-29 in SEQ ID NO: 2 or amino acids at positions 20-31 in SEQ ID NO: 1 are DYKDDDDK (FLAG-tag sequence, SEQ ID NO: 49). Typical examples include ALuc34.

As used herein, "copepod luciferase" refers to a bioluminescent enzyme (luciferase) produced by tiny Crustaceans, luminescent plankton called "copepods." Specific examples include MoLuc1, MoLuc2, PaLuc1, PaLuc2, LoLuc, HtLuc1, HtLuc2, HmLuc1, HmLuc2, *Gaussia* luciferases (GLuc), and copepod luciferases (MLuc, MpLuc1, MpLuc2). The substrate specificity of copepod luciferases is that the luciferases specifically oxidize "coelenterazine." Typically, copepod luciferases catalyze a luminescent reaction in the deep-sea environment, specifically, at an optimum pH of about 7.5 to 8 and at an optimum temperature of about 4 to 10° C. (enzymatic properties), but also extensively catalyze luminescence reactions under different conditions. As used herein, "copepod luciferase" refers to a luciferase having an enzyme activity and structure in common with luciferases derived from known copepods. Specifically, the copepod luciferase in the present specification has enzyme activity for catalyzing a luminescent reaction at an optimum pH of about 5 to 8 and at an optimum temperature of about 4 to 25° C. in the presence of coelenterazine serving as a substrate, and the luciferase has two enzyme activity domains and a secretion signal at N-terminus, with a molecular weight of about 20 kD (18 kD-28 kD), which is the smallest among bioluminescent enzymes.

The "coelenterazine" is not limited to native coelenterazine (native CTZ, n CTZ), and also encompasses a variety of derivatives of native coelenterazine. Specifically, "coelenterazine" can also be referred to as "coelenterazines." Specific examples of coelenterazine include native coelenterazine (native CTZ), coelenterazine ip (CTZ ip), coelenterazine i (CTZ i), coelenterazine hcp (CTZ hcp), coelenterazine 400A (CTZ 400A), coelenterazine fcp (CTZ fcp), coelenterazine cp (CTZ cp), coelenterazine f (CTZ f), coelenterazine h (CTZ h), and coelenterazine n (CTZ n).

2. Luminescent Performance Evaluation on Optimum Luminescent Substrate of the Present Invention Used for Artificial Luciferase (ALuc)

(2-1) Enzyme Activity Confirmation Method

The enzyme activity of ALuc in the presence of an optimum luminescent substrate can be examined, for example, according to the following method.

First, using a known lipid reagent for gene introduction, a eukaryotic cell expression vector (e.g., pcDNA3.1(+)) encoding ALuc is introduced into African monkey-derived COS-7 cells; as a control, an expression vector encoding a known copepod bioluminescent enzyme is also introduced in the same manner. At a predetermined time (from 10 to 20 hours, for example, 16 hours) after the introduction of the vector, the cells are individually dissolved in a known cell lysis solution.

An example of base sequences encoding ALuc is shown by the sequence number.

Thereafter, the cell lysis solution is mixed with a known buffer solution containing the optimum luminescent substrate of the present invention, and its color intensity, temporal stability in luminescence, etc., are measured.

The luminescence intensity may be determined by measuring the intensity at a specific wavelength using a known luminescence spectrophotometer after the addition of the optimum luminescent substrate of the present invention. Measuring the luminescence intensity every minute shows the temporal change in luminescence to thereby enable the evaluation of luminescence stability. To measure a shift to red light, the entire wavelength is scanned.

As described above, the substrate of the present invention exhibited 100 to 10,000 times higher selectivity to artificial luciferases (ALuc) developed by the present inventors than to known marine animal-derived luciferase. This indicates that the use of the optimum luminescent substrate of the present invention provides assurance of luminescence specificity in various bioassay systems using ALuc.

Hereinafter, a "reporter analysis method in which the optimum luminescent substrate for ALuc is usable" in the present invention is categorized into three groups: "basic," "inducible," and "activatable," which are disclosed in Non-patent Literature 16 by Niu et al. Herein, the "basic" method is the simplest reporter analysis system in which ALuc is linked with each subject protein for labeling. Typical examples include a bioluminescent enzyme fusion protein linked with an antibody (i.e., bioluminescent enzyme label antibody). The "inducible" method differs from the "basic method" in that the expression of the reporter is controlled by a promoter. Typical examples include so-called reporter gene assays and two hybrid assays (reporter is expressed depending on stimulus) in addition to a bioluminescence resonance energy transfer (BRET) method. The "activatable" method is a reporter analysis method utilizing the mechanism wherein the reporter itself actively reacts in response to ligand stimulation to illuminate. Typical examples include integrated-molecule-format bioluminescent probe and bioluminescent capsule. This method can also be applied to protein complementation assay (PCA), protein splicing assay (PSA), etc.

(2-2) Basic Method

When the ALuc of the present invention is applied to a "basic method" as a reporter protein, a fusion protein may be prepared by simply linking the ALuc to a target protein. The basic method differs from other reporter analysis methods in that expression during the preparation of the fusion protein is performed by using an uncontrollable promoter.

In the present specification, the "fusion protein" includes (i) a fusion protein integrally expressed from a gene encoding a fusion protein containing a reporter protein, which is ALuc, and a target protein or a peptide recognizing the target protein; and (ii) a fusion protein obtained by separately expressing a reporter protein, which is ALuc, and a target protein or a peptide recognizing the target protein, and linking them by a chemical reaction. Examples of the means for linking separately expressed proteins, etc., by a chemical reaction include linking using a cross linker, linking using an avidin-biotin binding ability, binding using chemical reactivity of amino acid residues, and the like.

A bioluminescent fusion protein that binds to a typical antibody is hereby explained. A bioluminescent fusion protein is completed by producing a chimera DNA in which an ALuc gene is linked with the upstream or downstream of cDNA of antibody single chain variable fragment (scFv), and introducing the DNA into a suitable expression vector.

(2-3) "Inducible" Method

Application of a bioluminescent enzyme to an "inducible method" as a reporter protein has been employed for analyzing the expression timing and expression amount of genes obtained upon the production of recombination protein using recombinant DAN technology. In particular, a bioluminescent enzyme has been widely used as an index indicating the expression timing and expression amount change in response to external stimulus. Examples of analysis systems included in "inducible methods" include reporter gene assays, yeast two-hybrid assays, mammalian two-hybrid assays, protein splicing assays (PSA), protein complementation assays (PCA), circular permutation assays, bioluminescence resonance energy transfer assays (BRET), and the like. Use of ALuc as a reporter gene essential for these analysis systems remarkably improves assay measurement performance.

Hereinafter, the reporter gene assay and the two-hybrid assay, which are typical "inducible method" analysis systems, are explained in detail.

(i) Reporter Gene Assay

Although reporter gene assays have been widely used as means for analyzing activation of transcription factors in response to external stimulus and gene expression regulation, they are typically used for detecting endocrine disruptors (environmental hormones) that disturb signal transduction via nuclear receptors. The expression of a target gene (e.g., hormonal response gene) involving signal transduction via nuclear receptors is caused when the complex of a ligand and a receptor binds to a cis region (hormone-response element) that regulates the transcription of the gene. This is an assay in which a plasmid that contains a reporter gene such as luciferase at the downstream of the cis region of each hormone-response gene is introduced into cells, and the amount of the hormone molecule, which is to be a ligand, or the amount of the endocrine disruptor is detected by the intensity of bioluminescence.

Examples of host cells used herein include yeast cells, bacteria cells such as *Escherichia coli*, and insect cells, as well as mammalian cells such as COS cell, CHO-K1 cell, HeLa cell, HEK293 cell, and NIH3T3 cell used for general gene recombination. The present invention is mainly used in mammals, such as humans in vivo, or in mammalian cells in vitro.

In the reporter gene assay, firefly luciferase that has been widely used has the following drawbacks: (i) due to its large molecular weight, the maturation of expressed mRNA takes a long period of time, thereby imposing a great burden on the host cells, and (ii) due to the low luminescence intensity of firefly luciferase, it generally takes 1 to 2 days after stimulation to obtain a sufficient accumulation of luciferase (reporter). However, by selecting ALuc as a reporter protein, these problems are overcome.

Since the use of the luminescent substrate of the present invention with ALuc as a reporter protein ensures a significantly high luminescence intensity of the reporter, it has an advantage of very early stage measurement after the stimulation. Accordingly, the measurement time can be greatly reduced compared to conventional reporter proteins while ensuring high temporal stability in luminescence, thereby enabling luminescence measurement even for a cell strain with insufficient gene introduction. Further, since the red-shifted luminescence allows its improved transmittance through the plasma membrane or skin, the background intensity level is reduced, and high measurement accuracy can be achieved.

More specifically, ALuc, together with the luminescent substrate of the present invention, is employed in these reporter gene assays in such a manner that the bioluminescent enzyme is linked to a known eukaryotic cell expression vector containing a special promoter in an upstream portion, and the vector is then introduced into a eukaryotic cell. After a predetermined time, the measurement of bioluminescence is performed either in the presence or absence of signal (stimulation) (Non-patent Literature 20). The known pTransLucent vector can be used as this expression vector for reporter gene assay that can carry the ALuc of the present invention; the ALuc can easily be incorporated therein using a known method.

(ii) Two-Hybrid Method

The two-hybrid method is one of the techniques for discovering protein-protein interactions. In 1989, a yeast two-hybrid (Y2H) system using a *Saccharomyces cerevisiae* yeast was first established. This method utilizes the fact that the DNA binding domain (GAL4 DBD) and the transcriptional activation domain (TA) of GAL4 protein, which is a transcriptional activator, are separable. Fused GAL4 DBD and protein A (bait) are expressed as a fusion protein, and simultaneously, fused transcriptional activation domain (TA) and protein B (prey) are expressed in the cell as a fusion protein. Thus, interaction between proteins A and B can be observed. When proteins A and B bind, DBD approaches TA and binds to the "UASG" base sequence, which promotes the expression of the reporter gene that is linked to the downstream of the sequence. If the reporter gene is luciferase, the compatibility of proteins A and B can be detected by monitoring bioluminescence in the presence of its specific substrate. This enables screening of protein and peptide that interact with protein A (bait). The protein B (prey) used herein can be supplied from an expression library.

Examples of host cells include, in addition to yeast cells, bacteria such as *Escherichia coli*, mammalian cells, and insect cells. Other than GAL4 DBD, which is a transcriptional activator derived from a yeast, "LexA" etc., which is a repressor protein derived from *Escherichia coli*, can be used. A DNA encoding such a protein is linked to a DNA encoding a bait protein (i.e., protein A described above) such as a ligand binding region of a ligand-responsive transcriptional regulator, and then linked to the downstream of a promoter capable of functioning in host cells. On the other hand, usable examples of the "transcriptional activation region of a transcriptional activator" include a GAL4 transcriptional activation region, an *Escherichia coli*-derived B42 acid transcriptional activation region, a herpes simple virus VP16 transcriptional activation region, and the like. A DNA encoding such a transcriptional activation region is linked to a DNA encoding a prey protein (i.e., protein B described above), and then linked to the downstream of the promoter capable of functioning in host cells.

Specifically, examples of the vector that has a DNA encoding a DNA binding region of transcriptional regulator GAL4 and that can use budding yeast as a host cells include plasmid pGBT9 (produced by Clontech), etc. Examples of the vector that has a DNA encoding a GAL4 transcriptional activation region and that can be used in budding yeast include plasmid pGAD424 (produced by Clontech), etc. Examples of the vector that has a DNA encoding a GAL4 DNA binding region and that can be used in mammalian cells include pM (produced by Clontech), pBIND (produced by Promega), etc. Examples of the vector that has a DNA encoding a simple herpes virus VP16 transcriptional activation region and that can be used in mammalian cells include pVP16 (produced by Clontech), pACT (produced by Promega), etc. Examples of the vector that has a DNA encoding a LexA DNA binding region and that can be used in mammalian cells include pLesA (produced by Clontech), etc. Examples of the vector that has a DNA encoding B42 and that can be used in mammalian cells include pB42AD (produced by Clontech), etc.

In this case, for example, a vector in which ALuc gene is inserted as a reporter gene into the downstream of the region (e.g., "USAG") to which GAL4 binds may be formed. In the case of mammalian hosts, by using a commercially available pG5Luc vector (Promega) or pFR-Luc vector (Stratagene), ALuc, together with the substrate of the present invention, can be easily used by a known method in place of firefly luciferase incorporated into the vector. The luciferase (ALuc) of the present invention can also be used in place of chloramphenicol acetyltransferase (CAT) of a commercially available pG5CAT vector (Clontech).

(2-4) "Activatable" Method

The analysis system carrying a bioluminescent enzyme as a reporter protein according to the "activatable" method has been also studied and developed by the present inventors as a "bioluminescent probe" technique. Examples of application of ALuc to a "bioluminescent probe" and an "intracellular imaging method" using the bioluminescent probe are explained below as typical examples of the "activatable" method. Before this explanation, the "luminescent fusion protein (bioluminescent capsule)" previously developed is explained. In addition, ALuc can be suitably used as a reporter protein used in protein complementation assays (PCA) and protein splicing assays (PSA), which are included in the "activatable" method. These methods may sometimes be referred to as bioluminescent capsule method or bioluminescent capsule assay in the present specification.

(i) Production of Luminescent Fusion Protein (Bioluminescent Capsule)

By binding a membrane localization signal (MLS) to the C-terminus of ALuc, the ALuc can be localized in the plasma membrane. Such a molecular design allows smooth supply of the substrate and oxygen, enabling visualization of stable bioluminescence with extremely high intensity. For the visualization, it is possible to insert a polypeptide or protein gene as a cargo between the ALuc and a nucleic acid encoding the signal peptide. This allows efficient transfer of the cargo protein to the plasma membrane surface, and makes the place where the protein is transferred illuminated. One typical example is as follows. When the DEVD sequence or IETD sequence responsive to cell death signal is inserted between proteins, the DEVD sequence or IETD sequence actively responds to the activities of caspase-3 or caspase-8 as signals at the cell death, and functions as a visualization system. The present inventors name the luminescent fusion protein with this structure a "bioluminescent capsule."

Compared to conventional bioluminescent probes, the bioluminescent capsule shows stable optical properties with remarkably high intensity, and is responsive to a specimen that cannot pass through the plasma membrane. The bioluminescent capsule has a structure in which a "membrane localization signal (MLS)" is linked to the "C-terminus of the bioluminescent enzyme" as a basic frame structure. Since the effect of a chemical causing a conformational change on the cell surface, such as a chemical inducing cell death, can be visualized as a conformational change in the plasma membrane surface, by this structure or even when ALuc is linked to a tandem to enhance the intensity of luminescence, easy observation is possible. Preferably, it is possible to insert between the MLS and the C-terminus of the bioluminescent enzyme, a polypeptide causing a conformational change in the plasma membrane surface, or the partial recognition sequence of the peptide, specifically, the full length or the partial recognition sequence of a G-protein-coupled receptor (GPCR) or c-SRC. Further, by inserting a polypeptide inducing cell death or the recognition sequence of the peptide as a cargo between the MLS and C-terminus of the bioluminescent enzyme, cell death can be visualized. More specifically, when a peptide sequence (generally 20 amino acids or less, preferably 10 amino acids or less) recognized by caspases, proteases (e.g., serine protease and cystein protease), or digestive enzymes (e.g., trypsin and amylase), for example, an amino acid sequence containing "DEVE" or "ISTD" used in Examples 1-7 is inserted as a cargo, cell death can be visualized by caspase-3 activities. Further, by linking a fluorescence protein or another bioluminescent enzyme as a cargo between the bioluminescent enzyme and MLS, the intensity of luminescence on the plasma membrane surface is increased as in the case where the bioluminescent enzyme together with the luminescent substrate of the present invention is linked in tandem, allowing easy observation of the plasma membrane form. Since this fusion protein even responds to a ligand that cannot pass through the plasma membrane, screening with respect to various stimulations is possible.

The bioluminescent capsule is a luminescent fusion protein in which a protein or polypeptide, which is intended to be expressed on the plasma membrane surface, is inserted between the membrane localization signal (MLS) and the C-terminus of ALuc. Typical examples include
(a) a luminescent fusion protein wherein a fluorescence protein or luciferase is inserted between the membrane localization signal (MLS) and the C-terminus of ALuc (the luciferase may be other ALuc), and
(b) a luminescent fusion protein wherein a polypeptide changing the conformation in the plasma membrane, or a polypeptide having or less amino acids, preferably 10 or less amino acids recognized by the polypeptide changing the conformation in the plasma membrane, is inserted between the membrane localization signal (MLS) and the C-terminus of ALuc. The polypeptide changing the conformation in the plasma membrane is particularly preferably a polypeptide inducing cell death, and more preferably a polypeptide having 20 or less amino acids containing the recognition sequence of caspases, i.e., "DEVD" or "ISTD."
(ii) Application to Bioluminescent Probe Further, by incorporating ALuc into the integrated-molecule-format bioluminescent probe (Non-patent Literature 4, Non-patent Literature 6, Non-patent Literature 9, Non-patent Literature 10, Patent Literature 1 to 4) or the two-molecule-format bioluminescent probe (Non-patent Literature 7 and Non-patent Literature 8), which are recited in the pending patents applied by the present inventors, the presence or absence of a ligand and the intensity of the ligand activity can be observed with high luminance. By comprising, as the probe components, (i) the bisected bioluminescent enzyme (N- and C-terminal fragments), and (ii) a ligand-binding protein responsive to the target ligand and (iii) a recognition protein that recognizes the interaction of the ligand with the ligand-binding protein, which are linked to the vicinity of the bisected bioluminescent enzyme, it is possible to form a high-performance bioluminescent probe. This bioluminescent probe functions such that, as the recognition protein recognizes the ligand binding of the ligand-binding protein, the two adjacent fragments of the bisected enzyme complement each other and thereby change the enzyme activity. Here, due to the high luminescence intensity and stability of the bisected enzyme, it is possible to perform reliable measurement with an improved detection limit.

In the present invention, "integrated molecule-format bioluminescent probe" denotes a known bioluminescent probe in which all components for visualization imaging are integrated in a single fusion molecule (disclosed in Patent Literature 1-2). For example, "integrated molecule-format bioluminescent probe" denotes a fusion protein that comprises, as fundamental components, the two fragments of N- and C-terminals obtained by bisecting ALuc, a ligand-binding protein, and a recognition protein for recognizing the ligand-binding protein. Similarly, "two molecule-format bioluminescent probe" in the present invention denotes a bioluminescent probe in which the two fragments of N- and C-termini obtained by bisecting ALuc are present in the fusion protein containing the ligand-binding protein, and in the fusion protein containing the recognition protein, respectively.

When ALuc is used for these bioluminescent probes, the ALuc must be bisected into an N-terminal fragment and a C-terminal fragment.

Patent Literature 1 to 4 discloses the details regarding the actual method for using ALuc as an integrated molecule-format bioluminescent probe. More specifically, ALuc is bisected, and a chimera DNA encoding a bioluminescent probe in which a ligand-binding protein and a peptide sequence, which recognizes the change in steric structure upon binding of a ligand to the protein, are tandemly linked. Generally, the chimera DNA is subcloned into a vector suitable for the cells in which the chimera DNA is intended to be expressed, and the vector is introduced into the cells to be expressed. However, the chimera DNA may be ligated to a control sequence at an upstream portion to be directly introduced into the cells. The target cells are preferably mammal-derived cells, such as human cells. Other suitable examples include cells that exist in a living subject, and culture cells that retain the native function, yeast cells, insect cells, and prokaryotic cells such as *Escherichia coli*. The type of the vector is also not particularly limited. A suitable vector capable of being expressed in the target host cells is appropriately selected. The introduction of the vector into the cells is performed using known transfection methods such as a microinjection method or an electroporation method, or a transfection method using a lipid (BioPORTER (Gene Therapy Systems, Inc.), Chariot (Active Motif), etc.).

Since the bioluminescent probe using the superluminescent enzyme together with the optimum luminescent substrate according to the present invention is introduced into cells as a chimera DNA and expressed in the cells as a fusion protein, by measuring the variance in light intensity emitted from the cells after subjecting the transformed cell to ligand stimulation, the property or levels of activity of the ligand may be evaluated.

When ALuc is incorporated in the bioluminescent probe, the "ligand-binding protein," which can be incorporated in the probe together with the ALuc, is intended to mean a protein that binds with a ligand at the ligand binding site. The ligand-binding protein may serve to, in response to the interaction with the ligand, for example, change the steric conformation, cause phosphorylation, or facilitate protein-protein interaction. Examples of such ligand-binding proteins include nuclear receptors (NR) to which such ligands as hormones, chemical substances, or signal transduction proteins bind; cytokine receptors; and various protein kinases. A suitable ligand-binding protein is selected depending on the target ligand. The ligand that binds to the ligand-binding protein is not particularly limited insofar as it binds to the ligand-binding protein. The ligand may be an extracellular ligand that is introduced in response to an extracellular stimulus, or an intracellular ligand that is produced inside the cells in response to the extracellular stimulus. Examples thereof include agonists or antagonists of the receptor protein (for example, nuclear receptor, or G-protein-coupled receptor), signal transduction proteins such as cytokine, chemokine, or insulin, intracellular second messenger, lipid second messenger, phosphorylated amino acid residue, G-protein-coupled receptor ligand, and like ligands that specifically bind to proteins involved in intracellular signal transduction.

For example, when the intracellular second messenger, the lipid second messenger, or the like is used as a ligand, the binding domain of each second messenger may be used as the ligand-binding protein. "Second messenger" denotes a different kind of the intracellular signal transduction substance that is newly produced as a result of the interaction of the extracellular signal transduction substance, such as a hormone or neurotransmission substance, with a receptor that exists in the plasma membrane. Examples of the second messengers include cGMP, AMP, PIP, $PIP_2$, $PIP_3$, inositol trisphosphate ($IP_3$), $IP_4$, $Ca^{2+}$, diacylglycerol, and arachidonic acid. For example, for $Ca^{2+}$ as the second messenger, calmodulin (CaM) may be used as the ligand-binding protein.

(iii) Intracellular Imaging

Further, using the gene encoding the ALuc enables stable introduction of the ALuc into various cell strains. For example, using the gene enables stable introduction of the ALuc into the undifferentiated embryonic cells, ES cells, novel induced pluripotent stem cells (iPS cells). Since the cell components do not emit light themselves, it has been very difficult to research the intracellular molecular phenomenon and tissue specificity of the cells. To address this difficulty, a molecular probe containing the ALuc is introduced into somatic cells before the embryo is formed, and then the embryo is differentiated into various tissues. This enables measurement of specific molecular phenomena in respective organs with high sensitivity.

This process is performed according to the method of Yamanaka et al. (Non-patent Literature 36).

Further, by linking the ALuc to a suitable signal peptide, the ALuc can be used for high luminance imaging of various organelles. For example, by linking a GAP-43-derived MLCCMRRTKQV sequence (SEQ ID NO: 52) to the N- or C-terminus of ALuc, the ALuc may be localized in the plasma membrane. Linking a GRKKRRQRRR sequence (SEQ ID NO: 53) to a terminus enables localization in the cytosolic compartment of cells. Further, for localization in the endoplasmic reticulum (ER) and the cellular nucleus, KDEL (SEQ ID NO: 54) and DPKKKRKV (SEQ ID NO: 55) sequences, respectively, are linked to a terminus. Furthermore, by linking to HIS-tag (HHHHHH) (SEQ ID NO: 48), FLAG-tag (DYKDDDDK) (SEQ ID NO: 49), Myc-tag (EQKLISEEDL) (SEQ ID NO: 50), HA-tag (YPYDVPDYA) (SEQ ID NO: 51), V5-tag (GKPIPNPLLGLDST) (SEQ ID NO: 556), T7-tag (MASMTGGQQMG) (SEQ ID NO: 57) or like antigen sites, the ALuc can be used for immunostaining or separation/refinement in acellular systems. In these usages, known immunostaining technologies or immunocytochemistry may be adopted.

[II] Determination of Reaction Solution Containing Luminescent Substrate of the Present Invention Used for Bioassay 1. Reaction Solution for Bioassay (1-1) Lysis Buffer (Cell Lysis Solution) and Assay Buffer (Reaction Solution)

Conventionally conducted bioassays involve two separate assay buffers: a buffer for lysis (cell lysis solution); and a buffer for assay (assay solution). This is because high lytic activity and low inhibitory effect on a bioluminescent enzyme are considered essential for quick lysis of the cells, whereas stable assay conditions and removal or analysis of self-luminescence inducing components to reduce background are considered essential for a bioassay reaction.

Promega Corporation has been selling a lysis buffer and an assay buffer under the respective trade names of Luciferase Lysis Buffer (catalog number: E291A) and Luciferase Assay Buffer (catalog number: E290A). New England Biolabs Inc. (NEB) has also been selling a lysis buffer and an assay buffer under the respective trade names of Luciferase Lysis Buffer (catalog number: B3321) and Luciferase Assay Buffer (catalog number: E3300S). Although neither Promega nor NEB discloses the formulations of their commercial products, both disclose complex protocols in which a lysis buffer and an assay buffer are separately used.

The following description describes a study on the formulations of the reaction solution components usable together with the optimum luminescent substrate for ALuc in the present invention.

(a) surfactant: polyoxyethylene octylphenyl ether (Triton X-100; TX100), Nonidet P-40 (NP40), polyoxyethylene sorbitan monolaurate (Tween20; TW20), polyoxyethylene sorbitan monooleate (TW80), polyoxyethylene cetyl ether (Brij58), sodium dodecyl sulfate (SDS), and the like. The degree of hydrophilicity is indicated as TW20>Brij58>TW80>TX100>NP40; and the degree of the power of surfactant is indicated as NP40>TX100>Brij58>TW20>TW80.

(b) salts: NaCl, KCl, $(NH_4)_2SO_4$, and the like (c) SH reagents: mercaptoethanol, DTT, and the like (d) polyols: glycerol, glucose, sucrose, and the like (e) glycols: polyethylene glycol (PEG), polypropylene glycol (PPG)

(f) chelate reagents: EGTA, EDTA, and the like (g) protease inhibitors: aprotinin (molecular weight: 6.5 kD), leupeptin (molecular weight: 427), pepstatin A (pepstatin, molecular weight: 686), phenylmethylsulfonyl fluoride (PMSF, molecular weight: 174), antipain (antipain, molecular weight: 605), chymostatin (chymostatin, molecular weight: 608), pefabloc SC (AEBSF, 240 Da), DFP (184 Da), p-APMSF (216 Da), STI (20,100 Da), leupeptin (460 Da), N-tosyl-L-phenylalaninechloromethylketone, 3,4-dichloroisocoumarin (215 Da), EDTA-$Na_2$ (372 Da), EGTA (380 Da), 1,10-phenanthroline (198 Da), phosphoramidon (580 Da), dithiobis (2-amino-4-methylpentane), E-(357 Da), cystatin, bestatin, epibestatin hydrochloride, aprotinin, minocycline, ALLN (384 Da), and the like (h) buffer agents: p-toluenesulfonic acid, tartaric acid, citric acid, phthalate, glycine, trans-aconitic acid, formic acid, 3,3-dimethylglutaric acid, phenylacetic acid, sodium acetate, succinic acid, sodium cacodylate, sodium hydrogen maleate, maleic acid, sodium phosphate, $KH_2PO_4$, imidazole, 2,4,6-trimethylpyridine, triethanolamine hydrochloride, sodium 5,5-diethylbarbiturate, N-ethylmorpho line, sodium pyrophosphate, tris(hydroxymethyl)aminomethane, bicine, 2-amino-2-methylpropane-1,3-diol, diethanolamine, potassium p-phenolsulfonate, boric acid, sodium borate, ammonia, glycine (glycine), $Na_2CO_3$/$NaHCO_3$, sodium borate, or a combination thereof (i) Others: sodium molybdate (stabilization of receptors), dithiothreitol (dithiothreitol, DTT) (reducing agent)

(1-2) Basic Reaction Solution Component 1 to which the Optimum Luminescent Substrate for ALuc of the Present Invention can be Added In the present invention, the HBSS buffer (Hanks' balanced salt solution) is used as a basic composition. An HBSS buffer was prepared in accordance with a known protocol (e.g., see the website of National Institute of Biomedical Innovation at http://cellbank.nibio.go.jp/legacy/sheet/att00011.htm), as described below.

First, the following four types of solutions are prepared beforehand, and mixed for use.

Solution 1: 1.4% NaHCO$_3$ solution

Solution 2: a solution prepared by dissolving 80.0 g of NaCl, 4.0 g of KCl, 2.0 g of MgSO$_4$.7H$_2$O, 0.6 g of Na$_2$HPO$_4$.2H$_2$O, 10.0 g of glucose, and 0.6 g of KH$_2$PO$_4$ in 800 ml of water Solution 3: a solution prepared by dissolving 1.4 g of CaCl$_2$ in 100 ml of water Solution 4: a solution prepared by weighing 0.4 g of phenol red, making it into a paste with a small amount of water, and adding water thereto to give 150 ml of a solution The mixture is adjusted to a pH of 7.0 with a sodium hydroxide solution (N/20) so as to give 200 ml.

For use, 2.5 ml of solution 1, 8 ml of solution 2, 1 ml of solution 3, and 1 ml of solution 4 are added to 87.5 ml of sterile water. When phenol red is not necessary, solution 4 can be omitted.

(1-3) Basic Reaction Solution Component 2 to which the Optimum Luminescent Substrate for ALuc of the Present Invention can be Added The Tris buffer refers to a widely used conventional buffer component (as used herein, "tris" is an abbreviation for tris(hydroxymethyl)aminomethane, which is typically prepared by adding HCl to 10 mM of a tris salt to thereby adjust the pH, and optionally adding 1 mM of EDTA thereto as an additive), and is used in a variety of biological studies because of its high biocompatibility. Nonetheless, there has been insufficient study of the effects of the Tris buffer on a bioluminescent reaction.

As the reaction solution in the present invention, a Tris buffer can be suitably used for bioluminescence, and can be a basic buffer component usable in both lysis and assay.

(1-4) Buffer Formulation in the Present Invention

The above-stated basic buffer components, an HBSS buffer and a Tris-buffer, are combined for use. These buffers are mixed at a ratio of 20 to 50:50 to 20, preferably 40 to 60:60 to 40, and most preferably 60:40 in volume % (v/v).

The surfactants NP-40, TW80, and SDS are combined for use. The NP-40, TW80, and SDS are mixed at a ratio of 1:0.1 to 1:0 to 0.5, preferably 1 to 2:0.5 to 2:0.1 to 1, and most preferably 1:1:0.1 in volume % (v/v).

The surfactant TW80 is mixed with other surfactants and the ratio is adjusted to be 1 to 10 volume % (v/v), and preferably 5 to 10 volume % (v/v).

For polyols, polyethylene glycol (PEG), and a sugar component (sucrose, glucose) are combined. PEG400 is contained in an amount of 0.01 to 10 volume % (v/v), and the sugar component (sucrose, glucose) is contained in an amount of 0 to 20 mg/mL. PEG400 is preferably contained in an amount of 0.1 to 10 volume % (v/v), and the sugar component (sucrose, glucose) is preferably contained in an amount of 2 to 10 mg/mL.

For heavy metals, Fe(III), Cu(II), Mo(VI), and Zn(II) can be contained singly or in a combination in a concentration within a range of 0.01 to 1 PPM, and preferably 1 PPM.

The halogen ions Br and I can be contained singly or in combination in a concentration of 1 to 100 mM, and preferably 50 to 100 mM.

It is further preferable to optionally add a reducing agent, such as vitamin C, to improve the luminescence stability.

From the above study, preferable buffer formulations as a one-shot reaction solution containing a luminescent substrate specific to ALuc were narrowed down as shown below.

Specifically, a basic formulation of "one-shot reaction solution" in a bioluminescent enzyme utilization technique, where prompt lysis and observation under high luminescent intensity are required, can be established by combining a Tris-HCl buffer, which is a basic buffer of the C3 buffer, with an HBSS buffer, and further combining a surfactant, NP-40 or SDS, salts such as Al(III), Ca(II), Cu(II), Fe(III), or Mg(II), PEG or PPG, a halogen ion (I, Br), and D(+)glucose or glycine.

4. Measuring Procedure and Measuring Apparatus Used in the Present Invention

The ligand activity can be measured in accordance with a typical bioluminescence assay, and conventional protocols can be used without any restriction.

Luminometers (e.g., Mini Lumat LB 9506, Berthold; and GloMax 20/20n, Promega) have typically been used to measure bioluminescence intensity. A cell lysis solution is poured over cultured cells in a plate to thereby produce a cell lysate. After the cell lysate is mixed with the optimum luminescent substrate of the present invention for ALuc, the luminescence intensity is immediately measured.

To measure the ligand activity of cultured cells in a 96-well plate, a ready-made bioluminescence plate reader (e.g., Mithras LB 940, Berthold; and SH-9000, Corona) can be used. Using a substrate solution autoinjector attached to the plate reader, a substrate can instantaneously be introduced, and bioluminescence generated by the expressed probe can instantaneously be measured in the presence of the ligand.

5. Analyte of Interest in Screening Method

Examples of analytes in these screening methods include organic or inorganic compounds (particularly compounds of low molecular weight), proteins having bioactivity, and peptides. These substances may be those whose function and structure are either known or unknown. A "combinatorial chemical library" can be an effective means as a group of analytes for efficiently identifying target substances. The preparation and screening of a combinatorial chemical library are well known in the art (see, e.g., U.S. Pat. No. 6,004,617 and U.S. Pat. No. 5,985,365). Alternatively, a commercially available library may be used (e.g., libraries available from ComGenex (US), Asinex (Russia), Tripos Inc. (US), ChemStar, Ltd. (Russia), 3D Pharmaceuticals (US), and Martek Biosciences). By applying a combinatorial chemical library to a cellular cluster for expressing a probe, a "high-throughput screening" can be carried out.

6. Kit

The present invention also provides a bioassay kit comprising the luminescent substrate specific to ALuc. The kit according to the present invention may optionally comprise various components for carrying out a bioassay. Examples of such components include, but are not limited to, bioluminescent enzymes, vectors comprising genes for encoding bioluminescent enzymes, cells for expressing bioluminescent enzymes, the luminescent substrate specific to ALuc according to the present invention, various instruments (96-well plates, and tubes), and control samples. The kit may also comprise a user manual describing the procedure for carrying out the bioassays according to the present invention.

Preferable examples of bioluminescent enzymes include bioluminescent enzymes derived from insects and marine animals, typically firefly luciferases, click beetle luciferases, *Renilla* luciferase, copepod luciferases (*Metridia longa* luciferase, *Metridia pacifica* luciferase), and the artificial luciferases (ALuc) previously developed by the present inventors. The artificial luciferases (ALuc) are particularly preferable examples.

A vector comprising a gene for encoding a bioluminescent enzyme can be produced in accordance with a known technique depending on the intended bioassay (e.g., reporter-gene assay, two-hybrid assay, protein complementation assay, intein-mediated protein splicing assay, and single-chain probe-based assay).

Examples of control samples include positive controls comprising a bioluminescent enzyme in a predetermined amount, and negative controls not comprising a bioluminescent enzyme.

The kit according to the present invention can be produced by combining the above-described components in accordance with a known technique. The kit according to the present invention can be used for carrying out the aforementioned bioassays of the present invention.

[III] Terms and Concepts Used in the Present Invention

The other terms and concepts used in the present invention are specifically defined in the descriptions of embodiments and examples of the invention. The terms are generally selected from the IUPAC-IUB Commission on Biochemical Nomenclature, or based on interpretations of idiomatic terms and words in the related field. Except for the techniques with apparent sources, the various techniques used to carry out the present invention can be easily and consistently performed by one of ordinary skill in the art with reference to published documents, etc. For example, genetic engineering and molecular biological techniques can be carried out according to J. Sambrook, E. F. Fritsch & T. Maniatis, "Molecular Cloning: A Laboratory Manual (2nd edition)," Cold Spring Harbor Laboratory Press, Cold Spring Harbor, N.Y. (1989); D. M. Glover et al. ed., "DNA Cloning," 2nd ed., Vols. 1 to 4, (The Practical Approach Series), IRL Press, Oxford University Press (1995); Ausubel, F. M. et al., Current Protocols in Molecular Biology, John Wiley & Sons, New York, N.Y., 1995; Japanese Biochemical Society ed., "Zoku Seikagaku Jikken Koza 1 [Continuation of Biochemistry Experimental Series 1], Idensi Kenkyu Ho [Gene Study Method] II" Tokyo Kagaku Dojin (1986); Japanese Biochemical Society ed., "Shin Seikagaku Jikken Koza 2 [New Biochemistry Experimental Series 2], Kakusan [Nucleic Acid] III (Kumikae DNA Gijutsu [DNA Recombinant Technology])," Tokyo Kagaku Dojin (1992); R. Wu ed., "Methods in Enzymology," Vol. 68 (Recombinant DNA), Academic Press, New York (1980); R. Wu et al. ed., "Methods in Enzymology," Vols. 100 (Recombinant DNA, Part B) & 101 (Recombinant DNA, Part C), Academic Press, New York (1983); R. Wu et al. ed., "Methods in Enzymology," Vols. 153 (Recombinant DNA, Part D), 154 (Recombinant DNA, Part E), & 155 (Recombinant DNA, Part F), Academic Press, New York (1987), etc.; the methods mentioned in the documents referenced in these documents; or other various similar methods and modified methods thereof that are substantially the same as the disclosed methods. The proteins, peptides, and DNAs encoding them used in the present invention are available from existing databases (e.g., URL: http://www.ncbi.nlm.nih.gov).

EXAMPLES

The following examples specifically describe the present invention in more detail; however, the present invention is not limited to the Examples.

The other terms and concepts used in the present invention are based on the interpretations of idiomatic terms and words in the related field. Except for the techniques with apparent sources, the various techniques used to carry out the present invention can be easily and consistently performed by one of ordinary skill in the art with reference to published documents, etc. The various analyses were performed in accordance with the methods disclosed in instruction manuals, catalogs, or the like of the analytical instruments, reagents, and kits used in the analyses.

The disclosures of the technical documents, patent publications, and specifications of pending patent applications cited herein are incorporated into the present specification by reference.

Example 1: Study on Phylogenetic Characteristics and Steric Structure of Artificial Bioluminescent Enzyme Although a series of artificial bioluminescent enzymes (ALuc) were synthesized as disclosed in the patent application earlier filed by the present inventors, the details of a luminescent substrate specific to ALuc have not been unveiled. Thus, the inventors first elucidated the genetic correlation between ALuc and other bioluminescent enzymes from the phylogenetics perspective.

Using CLUSTALW2.1, a multiple sequence alignment program for amino acid sequences provided by the National Center for Biotechnology Information (NCBI) in the United States, the sequence of ALuc was compared with those of *Metridia longa* luciferase (MLuc), *Metridia pacifica* luciferase 2 (MpLuc2), *Gaussia* luciferase (GLuc), and Lucia, which are typical marine animal-derived bioluminescent enzymes and are common in the use of coelenterazine as a substrate. The results revealed as shown in FIG. 1(A) that the sequence of ALuc is located in a lineage greatly different from known sequences. This genetic lineage characteristic strongly implicated that ALuc may have a luminescent-substrate specificity different from that of known luciferases. To prove the implication, the inventors decided to try unveiling the steric structure of ALuc to thereby discover a suitable structure of a substrate that matches the steric structure of ALuc.

To unveil the steric structure of ALuc, the following experiment was conducted. First, the conformation of the main chain of each amino acid residue found in the X-ray crystallographic data (PDBID: 2hpsA, 2hq8A) of coelenterazine-binding protein (CBP) was converted to the corresponding codes, specifically the following three forms, $\alpha$-helix (h), $\beta$-sheet (s), and other (o) in the manner disclosed in a related art document (Non-patent Literature 35) to describe the supersecondary structure.

Subsequently, CBP and ALuc 30 were compared in terms of the homology of the amino acid sequence, and the comparison found a homology of 16.7%. Amino acid sequences were then aligned based on the homology, and amino acid residues in the structural data of 2hpsA were substituted using MolFeat v4.5 (http://www.fiatlux.co.jp/product/lifescience/molfeat/mol-index.html) to thereby prepare a molecular model. Subsequently, insertion and deletion of amino acid residues were performed using HyperProtein v1.0 (http://www.hyper.com/Products/HyperProtein/tabId/504/Default.aspx) and Chem3D Ultra v8.0 (http://www.cambridgesoft.com/Ensemble_for_Chemistry/ChemBio3D) along the alignment to achieve a supersecondary structure match, including coelenterazine. In this manner, a molecular modeling was cautiously performed.

Finally, molecular mechanics (MM) calculation using the Polak-Ribiere algorithm was performed to optimize the structure.

The technique described above unveiled the steric structure of ALuc30 (FIG. 1B). The results indicate that ALuc30 is composed of nine α-helices, and the helices surround a luminescent substrate (the red compound at the center). The substrate is composed of an imidazole frame structure with three residues (i.e., R-A, R-B, and R-C), and pierced through ALuc from the R-A side into the back. R-A is in the form of a bent arrow tip, and space is present around R-A. R—B is pierced into the upper side turning against R-A, and is surrounded by hydrophobic amino acids. R—C is located near the entry of the pocket of the bioluminescent enzyme and interacts with an amino acid of the C-terminus of ALuc30 (e.g., the ninth helix).

Example 2: Study on Chemical Structure of Coelenterazine Derivatives

Figure 2:
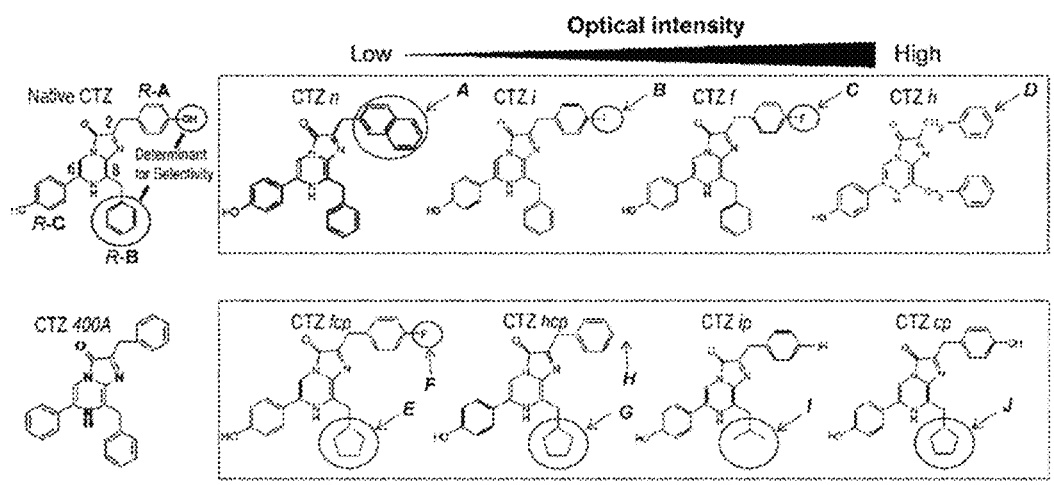
FIG. 2 The chemical structure of the coelenterazine derivatives used in this study. The upper part shows coelenterazine derivatives having a different R-A site. The lower part shows coelenterazine derivatives having a different R-B site. The arrows and circles indicate characteristic functional groups of the derivatives.

Based on the steric structure of ALuc revealed by Example 1, a study was conducted to find an appropriate chemical structure of coelenterazine derivatives that matches the steric structure (FIG. 2). FIG. 2 shows the chemical structure of native coelenterazine in the upper-left part. The upper part lists the chemical structures with the focus on the functional group of residue A (R-A). The lower part lists the chemical structures with the main focus on the functional group of residue B (R-B). The circles and arrows are added to show the difference of residues and functional groups.

Coelenterazine consists of an imidazole frame structure and three resides bound to the imidazole structure (herein, "R-A," "R-B," and "R-C"). The specificity of luciferases appears to be attributed to the structure of the residues and their functional groups.

In native coelenterazine, the R-A and R-C sites have a phenol structure, and the R-B site has a benzene structure. As apparent from the steric structure shown in FIG. 1B, a wide space is present near R-A; thus, R-A can allow a relatively large functional group to bind thereto. With this point in mind, a series of luminescent substrates were selected from coelenterazine derivatives on the basis of the size of the functional group bound to R-A (the parts indicated with arrows in the upper part of FIG. 2). From the hydrophobic environment around R-B, a residue capable of forming n-n stacking was assumed to be essential for a luminescent substrate specific to ALuc. To prove this assumption, substrates whose R-B residue was not a benzene ring (the lower part of FIG. 2) were selected from coelenterazine derivatives, and compared with substrates whose R-B residue is a benzene ring (upper part of FIG. 2) in terms of luminescence intensity.

Example 3: Comparison of Bioluminescence Intensity of ALuc Using Coelenterazine Derivatives To find a luminescent substrate specific to ALuc, the following experiment was conducted on the basis of the findings in the preceding Examples.

Figure 3A:
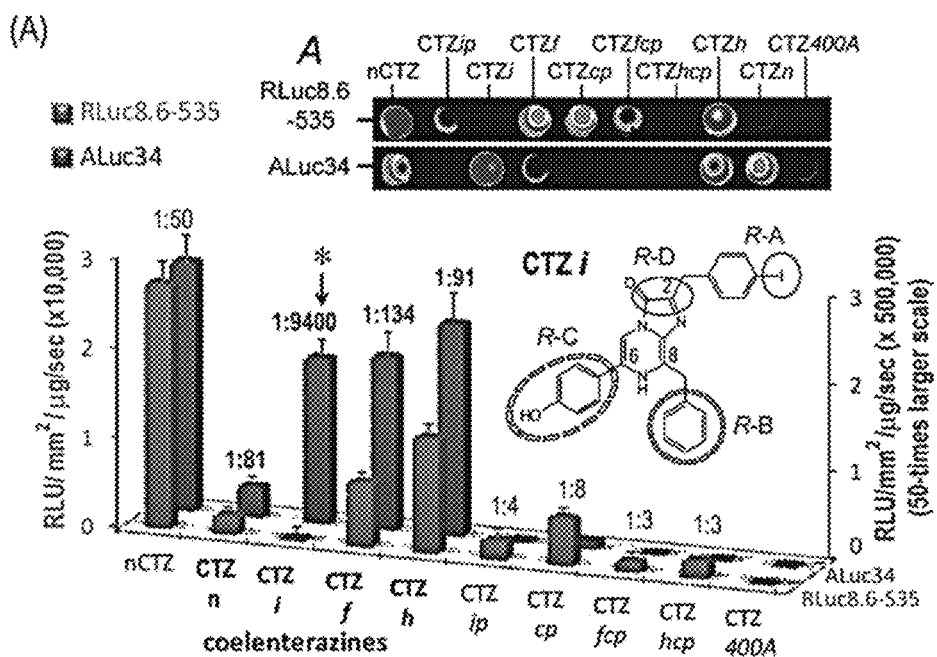
FIG. 3A Comparison between ALuc and RLuc8.6-535 in terms of luminescence intensity and spectrum in the presence of coelenterazine derivatives. (A) Comparison of luminescence intensity dependent on coelenterazine derivatives. The blue bar and Y axis in blue (left) represent RLuc8.6-535, and the red bar and Y axis in red (right) represent ALuc34. The inserted Fig. A shows the image of luminescence intensity dependent on coelenterazine derivatives.

First, African monkey kidney-derived culture cells COS-7 were cultured in a 96-well plate until the culture area covered 90% of the lower area of the plate. At this stage, the plate wells growing cells were divided into two groups, and pcDNA3.1(+) vector, which expresses ALuc34 or RLuc8.6-535, was introduced into each group by the lipofection technique (TransIT-LT1), followed by further incubation for 16 hours. After incubation, the cells were lysed and an aliquot of the lysates (10 μL) is placed in a fresh 96-well plate. Different luminescent substrates were simultaneously added thereto using a multichannel pipette, and the relative luminescence intensity was immediately measured with a luminescence imaging analyzer LAS-4000 (FujiFilm). FIG. 3A and Table 1 show the results. As seen in the results, the luminescence intensity varies depending on the size of the R-A site (e.g., comparison between CTZ n, CTZ i, CTZ f, and CTZ h). When the functional group of R-A is a halogen atom, a particularly higher substrate selectivity was observed (for CTZ 1:9400, for CTZ f, 1:134). As used herein, "substrate selectivity" refers to a luminescence intensity of ALuc compared with the luminescence intensity of RLuc8.6-535 in the presence of the same luminescent substrate. The inserted Fig. A shows a pseudo-colorimage of bioluminescence captured with LAS-4000.

Luminescent substrates having a residue other than a benzene ring at the R-B site exhibited typically weak luminescence intensity and selectivity (e.g., comparison between CTZ ip, CTZ cp, CTZ fcp, and CTZ hcp).

To demonstrate that the R-C site is preferably phenol (hydroxybenzene) (the speculation made in the preceding Examples), CTZ400A and CTZ h were compared in luminescence intensity. The comparison revealed that when the R-C site did not have phenol (hydroxybenzene) (i.e., CTZ400A), luminescence intensity was almost not observed at all, which compares with the strong luminescence observed when the R-C site had phenol (hydroxybenzene) (i.e., CTZ h).

The experimental results indicate that the optimum luminescent substrate for ALuc preferably has a benzene ring structure at the R-A site, carrying an appropriate size of a functional group, more preferably a benzene ring structure having a halogen ion as a functional group, and particularly more preferably a benzene ring structure having iodine, fluorine, or chlorine. For R-B, a benzene ring structure is preferable. For R-C, a benzene ring residue having a hydrophilic functional group (e.g., hydroxyl group, and thiol group) is preferable, and a phenol (hydroxybenzene) structure is more preferable.

Figure 3B:
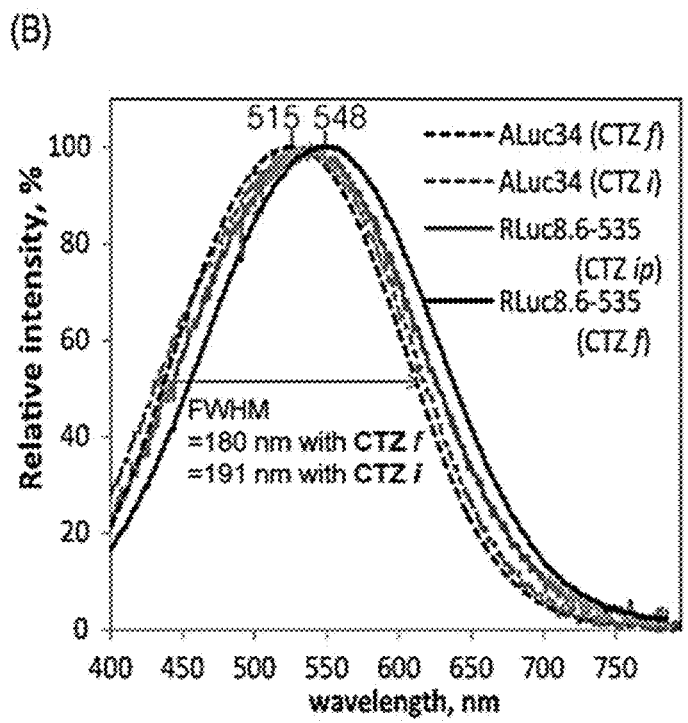
FIG. 3B Comparison between ALuc and RLuc8.6-535 in terms of luminescence intensity and spectrum in the presence of coelenterazine derivatives. (B) Comparison between ALuc and RLuc8.6-535 in terms of luminescence spectrum dependent on coelenterazine derivatives.

The bioluminescence spectrum of a cell solution (lysate) prepared in the same manner as in Example 3A was studied. First, 5 μL of the lysate was mixed with 30 μL of the luminescent substrate shown in FIG. 3B and immediately measured with a highly sensitive spectrophotometer (AB-1850, ATTO), which is capable of simultaneously detecting all of the wavelengths.

The spectrum analysis revealed that RLuc8.6-535 emits light at a wavelength that is red-shifted for about 30 nm, compared to ALuc34 when the same luminescent substrate is used. The analysis also revealed that ALuc34 emits light at a wavelength slightly more red-shifted when CTZ i is used than when CTZ f is used (Table 2).

TABLE 1

Comparison in Luminescence Intensity

| | RLuc8.6-535 | | ALuc34 | | Ratios |
|---|---|---|---|---|---|
| | ave | SD | ave | SD | (A34/RLuc8.6-535) |
| CTZ ip | 2200 | 969 | 8379 | 2833 | 4 |
| CTZ i | 97 | 31 | 913540 | 99031 | 9398 |
| CTZ f | 7151 | 931 | 956530 | 186595 | 134 |
| CTZ op | 5354 | 567 | 40564 | 9739 | 8 |
| CTZ fcp | 1217 | 501 | 3712 | 2349 | 3 |

TABLE 1-continued

Comparison in Luminescence Intensity

| | RLuc8.6-535 | | ALuc34 | | Ratios |
|---|---|---|---|---|---|
| | ave | SD | ave | SD | (A34/RLuc8.6-535) |
| CTZ hcp | 2058 | 616 | 5191 | 1379 | 3 |
| CTZ h | 12812 | 1481 | 1168658 | 216208 | 91 |
| CTZ n | 2132 | 635 | 172323 | 28977 | 81 |
| CTZ 400 | 3 | 16 | 11624 | 2965 | 3610 |
| | RLU/μg/sec/mm2 | | RLU/μg/sec/mm2 | | |

TABLE 2

Comparison in Spectrum Peak

| | ALuc34 | RLuc8.6-535 |
|---|---|---|
| CTZ f | 515 | 547 |
| CTZ h | 519 | 545 |
| CTZ i | 526 | — |
| CTZ ip | — | 535 |
| | wavelength, nm | |

Example 4: Study on Correlation Between ALuc Substrate Selectivity and Steric Structure Typically, bioluminescence is produced by luciferase-catalyzed oxidation of a luciferin. While a wide variety of luciferases are known, the chemical structure of luciferins is not so diverse. The number of luciferins used for marine animal-derived bioluminescent enzymes is also quite limited, and typical examples of such luciferins include coelenterazine and Cypridina luciferin. In particular, coelenterazine is commonly used for many marine animal-derived bioluminescent enzymes, and thus to date about 50 or more coelenterazine derivatives have been synthesized (Non-patent Literature 30 and 31).

Coelenterazine is composed of an imidazole frame structure and three residues bound to the frame structure (R-A, R-B, and R-C). The structure of each residue and its functional group are considered to be attributable to luciferase specificity.

Figure 4A:
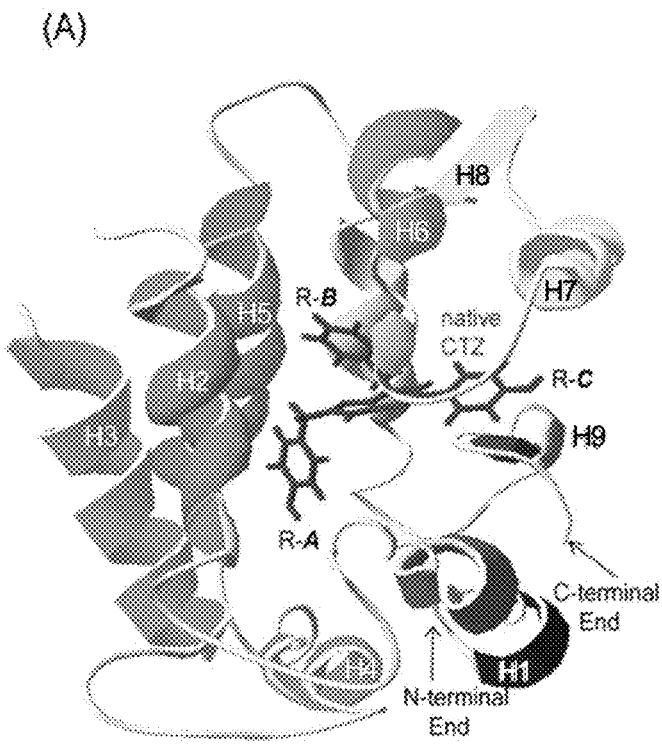
FIG. 4A Correlation between the substrate selectivity and the steric structure of ALuc. (A) The figure shows the supersecondary steric structure of ALuc30. The central part shows the frame structure of coelenterazine.
Figure 4B:
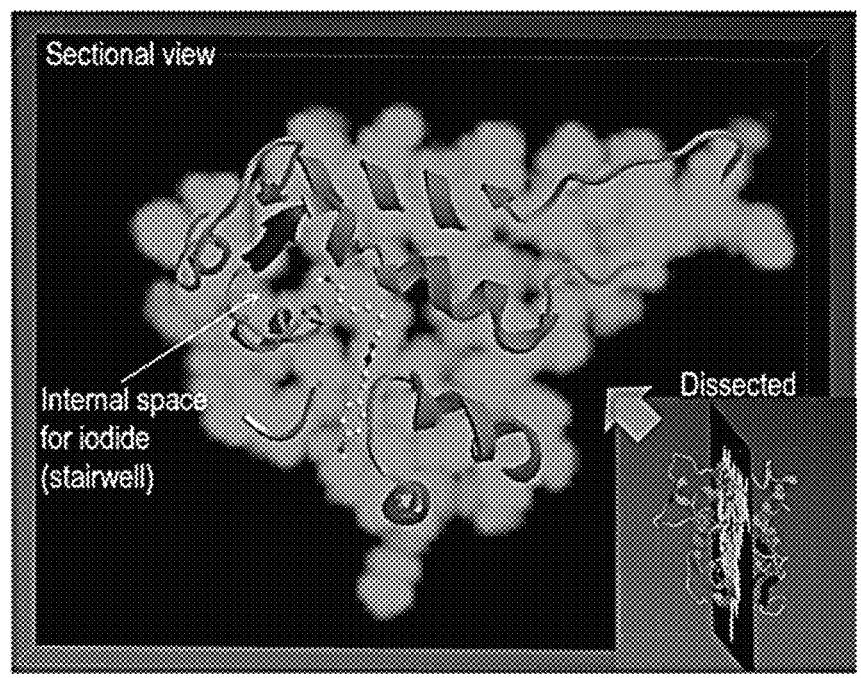
FIG. 4B Correlation between the substrate selectivity and the steric structure of ALuc. (B) The figure shows the internal profile of the steric structure of ALuc30. Internal space is present at the tip of R-A. A corresponding monochrome inversion image is also shown.
Figure 4B:
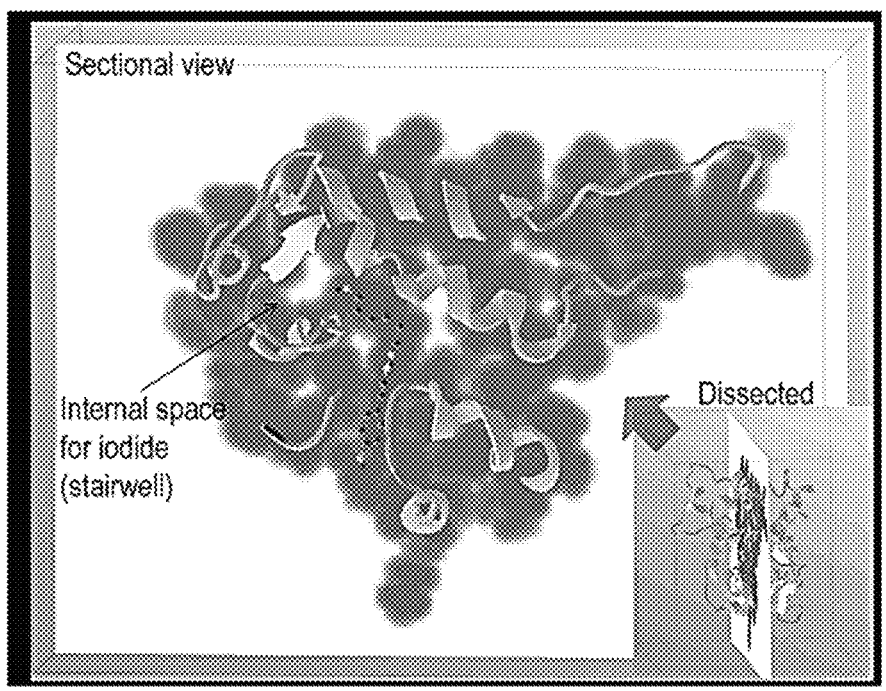

Native coelenterazine has a phenol structure in the R-A and R-C sites, with a benzene structure at the R-B site (FIG. 4A). As unveiled in the preceding Examples, the benzene structure of R-A has space that can accept a relatively large functional group. To confirm this feature, the internal part of the steric structure of ALuc30 was elucidated (FIG. 4B). As indicated with the white arrow, some space is present; the steric structure explains that a functional group bound to R-A can be relatively large. In particular, as is clear from the case of CTZ i, when the functional group is iodine, almost about 10,000-fold higher luminescent substrate selectivity is observed. This strongly suggests that the high selectivity is due to the "size effect" of the steric structure.

Iodine is typically an element that is less frequently present in protein in living organisms and is also an electron donor. This fact strongly suggests that the surprising bioluminescent enzyme selectivity exhibited by CTZ i is due not only to the size effect but also the suitable interaction between iodine as an electron donor and amino acids in ALuc.

Example 5: Luminescence Detection by Dual Assay in the Presence of Both ALuc and Cypridina Luciferase (CLuc)

Figure 5:
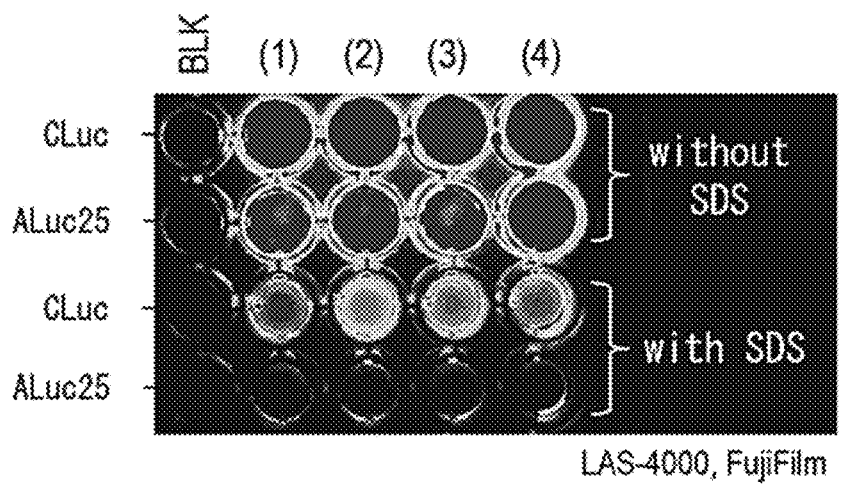
FIG. 5 The figure shows the results of a dual assay. Because SDS substantially deactivated the luminescence activity of ALuc, only the luminescence activity of CLuc remained. The following table shows the quantitative value of the luminescence intensity.
Figure 5:
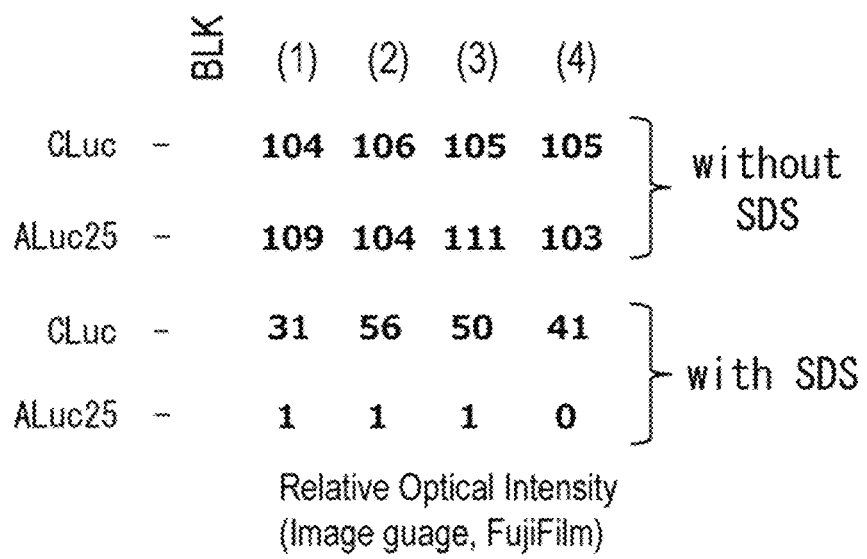

It is advantageous for simultaneous measurement of multiple biomarkers if a dual assay can be performed in the presence of two or more bioluminescent enzymes. With this point in mind, luminescence was measured in the presence of two bioluminescent enzymes (ALuc and CLuc) (FIG. 5). First, COS-7 cells were cultured in a 96-well plate, and a plasmid that expresses ALuc or CLuc was transfected into each cellular compartment by lipofection. Under the conditions, CLuc is secreted, but ALuc largely remains inside the cells because of the endoplasmic reticulum localization signal (KDEL) attached to the terminus. 16 hours later, 10 μL of the CLuc culture solution was mixed with 2 μL of ALuc lysate. Then, the luminescence intensity was compared between the cases where 0.1% SDS was added or not. After addition of the luminescent substrates specific to ALuc and CLuc, respectively.

Both CLuc and ALuc exhibited high luminescence intensity in the absence of 0.1% SDS (FIG. 5, the two rows from the top); however, in the presence of 0.1% SDS, while the light was mostly quenched with ALuc, CLuc somewhat maintained luminescence activity (FIG. 5, two rows from the bottom). The results indicate that even in a dual assay where two bioluminescent enzymes are present, the luminescence activity of the two different enzymes can be simultaneously measured by following the procedure: (1) measuring enzyme 1, (2) deactivating enzyme 1 by using SDS, and (3) measuring enzyme 2.

INDUSTRIAL APPLICABILITY

By using the present invention for ligand measurement based on a reporter-gene assay, which has hitherto been widely used, or as a luminescent substrate exclusively used for ALuc in a known bioluminescent probe, it becomes possible to exponentially improve measurement performance during assay. Therefore, the present invention can be used for various applications, including the development of a diagnosis reagent for basic biology research, medical and pharmaceutical purposes, or analytical chemistry.

The invention claimed is:

1. A method for detecting luminescence comprising
   (a) contacting a compound of formula (1) with polypeptide (B), and
   (b) measuring the intensity of luminescence generated by the contact, wherein formula (1) is:

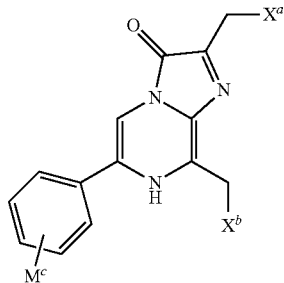

wherein $X^a$ represents a phenyl group optionally substituted with halogen or a naphthyl group, $X^b$ represents a phenyl group, and $M^c$ represents hydrogen, hydroxy, or thiol, and wherein polypeptide (B) has a copepod luciferase activity and is chosen from the group consisting of:

(i) the amino acid sequence of SEQ ID No: 1; and (ii) the amino acid sequence of SEQ ID No: 1 in which one or more amino acids are deleted in at least one of a region corresponding to positions 1-31 and a region corresponding to positions 217-221.

2. A kit for measuring bioluminescence comprising
   (a) a compound represented by formula (1)

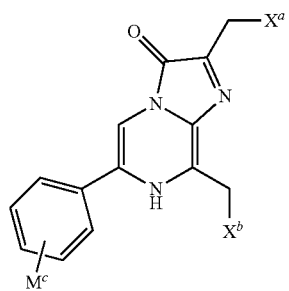

wherein $X^a$ represents a phenyl group optionally substituted with halogen or a naphthyl group, $X^b$ represents a phenyl group, and $M^c$ represents hydrogen, hydroxy, or thiol and (b) a polypeptide having a copepod luciferase activity chosen from the group consisting of:

(i) the amino acid sequence of SEQ ID No:1, and (ii) the amino acid sequence of SEQ ID No: 1 in which one or more amino acids are deleted in at least one of a region corresponding to positions 1-31 and a region corresponding to positions 217-221.

3. A method comprising the method according to claim 1, further in combination with one or more additional bioluminescent enzymes.

4. The method according to claim 1, which is a reporter gene assay, a two-hybrid assay, a bioluminescent capsule assay, or an integrated-molecule-format bioluminescent probe measurement method.

5. A bioluminescence resonance energy transfer (BRET) method comprising
(a) contacting a compound represented by formula (1) with polypeptide (B),
(b) allowing bioluminescent energy generated by the contact to transfer to another fluorescence protein, and
(c) measuring the luminescence intensity of the fluorescence protein to which the bioluminescent energy has transferred,
wherein formula (1) is represented by:

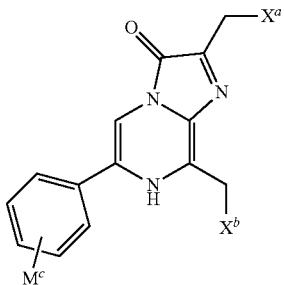

wherein $X^a$ represents a phenyl group optionally substituted with halogen or a naphthyl group,
$X^b$ represents a phenyl group, and
$M^c$ represents hydrogen, hydroxy, or thiol, and
wherein polypeptide (B) has a copepod luciferase activity and is chosen from the group consisting of:
(i) the amino acid sequence of SEQ ID No: 1; and
(ii) the amino acid sequence of SEQ ID No: 1 in which one or more amino acids are deleted in at least one of a region corresponding to positions 1-31 and a region corresponding to positions 217-221.

6. The method according to claim 1, wherein the compound represented by formula (1) is coelenterazine n (CTZ n), coelenterazine i (CTZ i), coelenterazine f (CTZ f), coelenterazine h (CTZ h), or coelenterazine 400A (CTZ 400A).

7. The kit according to claim 2, wherein the compound represented by formula (1) is coelenterazine n (CTZ n), coelenterazine i (CTZ i), coelenterazine f (CTZ f), coelenterazine h (CTZ h), or coelenterazine 400A (CTZ 400A).

8. The method according to claim 3, which is a reporter gene assay, a two-hybrid assay, a bioluminescent capsule assay, or an integrated-molecule-format bioluminescent probe measurement method.

* * * * *